US009885697B2

(12) United States Patent
Roizin et al.

(10) Patent No.: US 9,885,697 B2
(45) Date of Patent: Feb. 6, 2018

(54) SEMICONDUCTOR GAS SENSOR USING MAGNETIC TUNNEL JUNCTION ELEMENTS

(71) Applicant: Tower Semiconductor Ltd., Migdal Haemek (IL)

(72) Inventors: Yakov Roizin, Afula (IL); Menachem Vofsy, Kiryat Tivon (IL)

(73) Assignee: Tower Semiconductor Ltd., Migdal Haemek (IL)

( * ) Notice: Subject to any disclaimer, the term of this patent is extended or adjusted under 35 U.S.C. 154(b) by 171 days.

(21) Appl. No.: 14/958,037

(22) Filed: Dec. 3, 2015

(65) Prior Publication Data

US 2017/0160248 A1    Jun. 8, 2017

(51) Int. Cl.
*G01N 27/74* (2006.01)
*G01N 33/00* (2006.01)
(Continued)

(52) U.S. Cl.
CPC ......... *G01N 33/0065* (2013.01); *G01N 27/74* (2013.01); *G01N 33/0027* (2013.01);
(Continued)

(58) Field of Classification Search
CPC ............... G01N 27/74; G01N 33/0009; G01N 33/0027; G01N 33/0031; G01N 33/0062; G01N 33/0065
(Continued)

(56) References Cited

U.S. PATENT DOCUMENTS 8,826,726 B2    9/2014 Schmid et al.
9,097,677 B1    8/2015 Miller
(Continued)

OTHER PUBLICATIONS

Briand, Danick, "Thermally Isolated Microelectronic Devices for Gas Sensing Applications", M. Sc. in Engineering Physics, Ecole Polytechnique de Montreal, Institute of Microtechnology University of Neuchatel, Switzerland, 2001, 280 pages.
(Continued)

*Primary Examiner* — Benjamin Schmitt
(74) *Attorney, Agent, or Firm* — Bever, Hoffman & Harms, LLP

(57) ABSTRACT

A CMOS gas sensor that uses MTJ elements to capture/store gas concentration level data at high temperatures for later readout at low temperatures. Each MTJ element includes a storage layer whose magnetic orientation is switchable between parallel and anti-parallel directions relative to a fixed reference when heated above the storage layer's blocking temperature, whereby the MTJ element is switchable between low and high resistance states. During operation, reaction heat generated by a gas sensing element raises the MTJ element's temperature above the blocking temperature when ambient target gas exceeds a minimum concentration level, whereby an applied magnetic biasing force causes the storage layer's magnetic orientation to switch relative to the fixed reference, whereby the MTJ element captures measured concentration level data for later readout. In one embodiment, multiple MTJ elements connected in a NAND-type string switch at different concentration levels to provide highly accurate quantitative measurement data.

11 Claims, 9 Drawing Sheets

(51) Int. Cl.
  *H01L 43/08* (2006.01)
  *H01L 27/22* (2006.01)
(52) U.S. Cl.
  CPC .......... *G01N 33/0062* (2013.01); *H01L 27/22* (2013.01); *H01L 43/08* (2013.01)
(58) Field of Classification Search
  USPC ............... 73/25.01, 25.02, 25.05, 31.05
  See application file for complete search history.

(56) References Cited

U.S. PATENT DOCUMENTS

2005/0009211 A1* 1/2005 Linn ................. B82Y 10/00
  438/3
2005/0281081 A1  12/2005 Fullerton
2008/0151615 A1* 6/2008 Rodmacq ............ B82Y 25/00
  365/173

OTHER PUBLICATIONS

Socher, Eran, "Temperature Sensitivity of SOI-CMOS Transistors for Use in Uncooled Thermal Sensing", IEEE Transactions on Electron Devices, vol. 52, No. 12, Dec. 2005, pp. 2784-2790.
Rickart, M., et al. "Exchange coupling of bilayers and synthetic antiferromagnets pinned to MnPt", The European Physical Journal B (2005), 6 pages.

* cited by examiner

SEMICONDUCTOR GAS SENSOR USING MAGNETIC TUNNEL JUNCTION ELEMENTS

FIELD OF THE INVENTION

This invention generally relates to sensors capable of detecting a target gas in an environment, and more particularly to low-cost semiconductor gas sensors capable of determining concentration levels of a target gas.

BACKGROUND OF THE INVENTION

A gas sensor (aka, gas detector) is a device configured to detect the presence or absence of one or more target gases in a gaseous environment (e.g., a volume of air). For example, gas sensors are used to detect dangerous (e.g., flammable or toxic) gases in amounts that exceed minimum safety levels, or to detect oxygen depletion (i.e., when ambient oxygen levels fall below a predetermined concentration level). Gas sensors typically interface with a safety control system that performs a safety function in response to a positive detection signal generated by a gas sensor (e.g., to automatically shut down a process, or to sound a safety alarm, when the amount of target gas exceeds or falls below a predetermined concentration level).

Gas sensors capable of quantitatively measuring the concentration level of a target gas generally include remote-type gas sensors and contact-type gas sensors. Remote-type IR sensors, which include infrared (IR) point sensors and IR imaging sensors, are capable of detecting a target gas in a specified environment (i.e., the gas-filled volume containing the gas) without being in physical contact with the target environment, and are typically used to detect or measure gas leaks in large area environments such as oil refineries. However, remote-type gas sensors are typically expensive to produce and operate, and are thus impractical for detecting target gasses in smaller enclosed areas. In contrast to remote-type gas sensors, contact-type gas sensors are placed in direct contact with a monitored environment, and utilize gas sensing elements that react in a measurable way when a target gas is present in the environment. Contact-type gas sensors are typically smaller and less expensive than remote-type gas sensors, and are utilized mainly in enclosed areas such as buildings or processing chambers.

Semiconductor gas sensors are contact-type sensors including gas sensing elements whose electrical resistance changes in response to a reaction caused by the presence of a target gas, whereby detection or measurement of the target gas is achievable by way of monitoring changes in a current passed through the gas sensing element. The resistance change of gas sensing elements in semiconductor gas sensors is typically caused by one of three different reaction types: (i) a chemical reaction caused by changes in the composition or chemical structure of the gas sensing element in response to adsorption of the target gas into the gas sensing element; (ii) a temperature change of the gas sensing element as a result of endothermic or exothermic (e.g., combustion-type) reaction of the gas sensing element with the target gas; and (iii) a temperature change of the gas sensing element caused by a different thermal conductivity of the target gas versus ambient gases (this effect is dependent on gas flow over the sensing element). In both chemical-reaction-type gas sensors (i.e., semiconductor gas sensors configured in accordance with reaction type (i)) and in thermal-reaction-type gas sensors (i.e., semiconductor gas sensors configured in accordance with reaction types (ii) and (iii)), the resulting change in electrical resistance across the gas sensing element is measurable by way of passing a current through the gas sensing element, and monitoring the current for changes that are characteristic of reactions with the target gas.

Semiconductor gas sensors have an advantage over other gas sensor types is that they can typically be produced using low-cost photolithographic fabrication processes developed for integrated circuit (IC) fabrication, and are therefore smaller and less expensive than other gas sensor types. In many cases, semiconductor gas sensors utilize bulk Si or SOI wafers as starting materials, and include a thermally isolated membrane formed by removing silicon from the rear of the wafer by plasma or wet etching. The etch stops at the BOX of the SOI or at silicon nitride layer formed at the surface of bulk silicon. The gas sensing element, sensors and a resistive heater are typically formed on the membrane, and control circuitry of the gas sensor is typically fabricated on the adjacent bulk Si or SOI using known semiconductor processing techniques. Typical semiconductor gas sensor designs include close-membrane sensors and membranes suspended by holding arms, with the gas sensing element typically disposed in a center of the membrane to improve thermal isolation.

A problem with conventional chemical-reaction-type semiconductor gas sensors is that they require gas sensing elements that are limited to detecting one or a relatively small number of target gases. That is, the detection mechanism of chemical-reaction-type semiconductor gas sensors requires adsorption of the target gas into the gas sensing element material, and there is no gas sensing element material that is receptive to all gas types. Therefore, chemical-reaction-type semiconductor gas sensors are either limited to one target gas (or a very small number of target gasses), or must include multiple gas sensor units, each unit having a different gas sensing element materials, in order to detect more than one target gas type.

Two chemical-reaction-type semiconductor gas sensors have been proposed in which the gas sensing element is incorporated into a magnetic tunnel junction (MTJ) element. MTJ elements typically include two ferromagnetic electrodes separated by a thin insulating layer and configured such that a resistance across the MTJ element depends on the relative orientations of the easy axes of magnetization (herein "magnetic orientations" or "magnetic directions") of the two ferromagnetic electrodes. The magnetic orientation of one of the ferroelectric electrodes is typically fixed (e.g., using an adjacent antiferromagnetic layer) and acts as a reference layer of the MTJ element, while the second ferromagnetic electrode forms a "free" layer of the MTJ element whose magnetic orientation can be switched by an external magnetic field between parallel and anti-parallel magnetic orientations relative to the reference layer. When the magnetic orientations of the reference and free layers are parallel, a current conductance through the tunnel dielectric is relatively high (i.e., the MTJ element is in a low resistance state), and when the magnetization vectors are anti-parallel, the current conductance is low (i.e., the MTJ element is in a high resistance state). A first MTJ-type chemical-reaction-type semiconductor gas sensor was disclosed in U.S. Pat. No. 8,826,726 (University of California, 2014), where the free layer of a modified MTJ element was formed with a gas adsorbing magnetic material (cobalt) that was found to cause the magnetic orientation of the free layer to flip from anti-parallel (out-of-plane) to parallel (in-plane) when sufficient amount of a gas to be detected (hydrogen) gas was adsorbed, and where the modified MTJ element could be reset by heating the MTJ element to desorb the gas (i.e., heat is not used during the gas sensing phase). U.S. Pat. No. 9,097,677 (Univ. of Florida, 2015) discloses a second MTJ-based chemical-reaction-type semiconductor gas sensor in which two ferromagnetic structures are separated by a gas-sensitive metallic interlayer (e.g., palladium) such that a magnetic exchange coupling between the two ferromagnetic structures is affected by the amount of hydrogen gas adsorbed into the metallic interlayer. Similar to other chemical-reaction-type semiconductor gas sensors, MTJ-based chemical-reaction-type semiconductor gas sensors are limited in that they can only detect a limited number of gas types. Moreover, quantitative gas measurement using conventional MTJ-based chemical-reaction-type semiconductor gas sensor relies either on determining the time required for a single MTJ element to flip magnetic orientations, or determining magnetization vector angle changes when the temperature is switched from T1 to T2 value, with neither approach providing practical and sufficiently accurate quantitative measurement result data. Further, both U.S. Pat. Nos. 8,826,726 and 9,097,677 fail to specify cooling the MTJ elements to room temperature before measuring resistance in order to determine changes to the MTJ element's magnetic orientation.

Although not limited to a small number of target gasses like chemical-reaction-type semiconductor gas sensors, conventional thermal-reaction-type semiconductor gas sensors are insufficiently accurate in that they require measuring resistance changes at high temperatures. For example, combustion-type semiconductor gas sensors utilize catalyst-type gas sensing elements (e.g., Platinum or Palladium) that are heated to the threshold temperature of a combustible target gas, whereby the target gas exothermically reacts (oxidizes) to further increase the temperature of the catalyst-type gas sensing element to a reaction temperature, which is typically in the range of 100-350° C. Different target gasses have different threshold temperatures, so the catalyst-type gas sensing element is heated to different threshold temperatures at different times to detect different target gasses. Sensing of the reaction temperature increase is performed either by measuring current changes through the gas sensing element materials themselves (e.g., measuring resistance of a platinum catalyst), or by measuring the resistance of a sensor structure formed on the membrane adjacent to the gas sensing element (e.g., a specially formed MOSFET as taught, e.g., in D. Briand et al, IEEE EDL-22(I), pp. 11-13, 2001). Of these options, the special MOSFET approach currently provides the highest sensitivity (i.e., about 2%/° K at room temperature), with most other resistive sensor approaches exhibiting less than 0.5%/° K (IEEE Trans. ED vol. 52, 2005 "Temperature Sensitivity of SOI-CMOS Transistors for use in Uncooled Thermal Sensing", Eran Socher at al). However, in either case, the resistance measurement must take place during the exothermic reaction, which means that the measuring current must be passed through a measuring element (e.g., the special MOSFET or gas sensing element) that is close to the reaction temperature. Unfortunately, operation of the special MOSFET sensing transistor at high temperatures (above 150° C.) is limited due to leakage currents (even for partially or fully depleted SOI MOS transistors, where leakages are significantly lower than for the bulk devices). Moreover, the thermal sensitivity of the gas sensor's control circuit is strongly decreased at elevated temperatures (e.g., the thermal sensitivity of 0.35 μm transistors was observed as decreasing by approximately 50% at 100° C. as compared to room temperature).

What is needed is a low-cost thermal-reaction-type semiconductor gas sensor that avoids the high-temperature resistance measurement problems associated with conventional thermal-reaction-type semiconductor gas sensors. What is also needed is a low-cost gas sensor capable of quickly and accurately measuring the concentration level of a target (sensed) gas in a gaseous environment.

SUMMARY OF THE INVENTION

The present invention is directed to improved semiconductor gas sensors that implement various novel gas sensor arrangements to avoid problems associated with conventional semiconductor gas sensors, and to facilitate substantially faster and more accurate gas concentration level measurements. Each of the various novel gas sensor arrangements, which are set forth in exemplary embodiments described below, implement a core arrangement including one or more MTJ elements that is/are operably coupled to one or more gas sensing elements such that a resistance state of each MTJ element switches from a known initial (e.g., low) resistance value to an opposite (e.g., high) resistance value when its associated gas sensing element is exposed to target gas above a predetermined minimum concentration level, whereby each MTJ element effectively functions as a non-volatile memory cell capable of capturing one bit of target gas concentration level data (i.e., either above or below the predetermined minimum concentration level) that can be read out during a subsequent readout phase (i.e., by way of determining whether or not the resistance state of the MTJ element switched during the gas sensing phase). As set forth below with reference to exemplary embodiments, this core arrangement is modified in accordance with various novel sensor arrangements to produce, for example, thermal-reaction-type semiconductor gas sensors that avoid the high-temperature resistance measurement problems associated with conventional thermal-reaction-type semiconductor gas sensors, and semiconductor gas sensors that facilitate substantially faster and more accurate concentration level measurements of one or more target gases in a gaseous environment.

According to a first novel sensor arrangement, a thermal-reaction-type semiconductor gas sensor includes at least one MTJ element that is operably thermally coupled to a thermal-reaction-type gas sensing element such that reaction heat generated by the gas sensing element is utilized to switch the resistive state of the MTJ element(s) when a currently measured concentration level of the target gas exceeds a predetermined minimum gas concentration level. Similar to conventional MTJ elements, the sensor's MTJ element includes a high-coercivity reference layer separated from a low-coercivity storage layer by a thin insulating layer, the reference layer being configured to have a substantially permanent (first) magnetic orientation and the storage layer configured to have a (second) magnetic orientation that is switchable (changeable) between parallel and anti-parallel directions relative to the first magnetic orientation when a temperature of the MTJ element is above a storage blocking temperature of the storage layer. In addition, the gas sensing element is configured in a manner similar to gas sensing elements used in conventional thermal-reaction-type gas sensors such that reaction heat produced by the gas sensing element is generated in proportion to the concentration level of the target gas (i.e., either due to combustion of the target gas, or due to thermal conductivity of the target gas passing over the gas sensing element). According to an aspect of the first novel sensor arrangement, by way of the operable thermal coupling between the gas sensing element and the MTJ element, reaction heat generated by the gas sensing element is transferred to the MTJ element, whereby a temperature of the MTJ element (i.e., the "MTJ temperature") is at least partially controlled (e.g., increased) by the reaction heat. By way of configuring the gas sensing element and the MTJ element such that the amount of generated reaction heat increases the MTJ temperature above the blocking temperature only when a predetermined minimum concentration level of the target gas is present in the measured environment, the present invention provides a thermal-reaction-type gas sensor that utilizes the MTJ element as a non-volatile memory cell capable of capturing measured gas concentration level data at high reaction temperatures, and capable of storing the measured gas concentration level data such that it can be subsequently read out after the MTJ element has cooled to a lower (e.g., room) temperature, thereby avoiding the high-temperature resistance measurement problems associated with conventional thermal-reaction-type semiconductor gas sensors.

According to various alternative exemplary embodiments, gas sensors formed in accordance with the first novel sensor arrangement include additional features to further enhance gas sensor operations. One such feature is an MTJ element configuration in which both the reference and storage layers include both ferromagnetic and anti-ferromagnetic structures, which facilitates reliable and fast gas sensing operations by facilitating "fixed" (stable) magnetic orientations of the reference and storage layers in the absence of external magnetic fields. In a specific embodiment, the reference layer is formed with a reference blocking temperature that is above the sensor's normal operating temperature range and is thus effectively configured with a permanently fixed reference magnetic orientation, whereas the storage layer is formed with a substantially lower storage blocking temperature that is within the sensor's normal operating temperature range (e.g., in the range of 120-250° C.), whereby its storage magnetic orientation is made switchable during normal operation of the gas sensor. Another feature involves configuring the MTJ element such that the reference layer applies a spin torque transfer on the storage layer to facilitate switching the storage magnetic orientation without requiring a field line current to generate an external magnetic field, thereby reducing power consumption during sensor operations. Another feature is on-chip control circuit and associated connections configured to read the MTJ element's final resistance state at room temperature by way of waiting a suitable delay period after each gas sensing phase before generating a read current through the MTJ element, thereby providing optimal operating conditions for determining the MTJ element's final resistance value. Another feature is an on-chip field line structure that is operably magnetically coupled to the MTJ element, and is controlled by on-chip circuitry to generate an external magnetic field that serves as a magnetic bias force utilized during the gas sensing and/or reset phases of the sensor operating cycle, e.g., to fix the storage magnetic orientation in a parallel direction relative to the storage magnetic orientation. Yet another feature is an on-chip resistive heating element that is operably thermally coupled to the MTJ element(s) and associated control circuitry configured to generate control heat in amounts needed to optimize the MTJ element's temperature during one or both of the reset and gas sensing phases. According to yet another feature, frontend structures of the sensor's control circuit are fabricated on a bulk monocrystalline silicon substrate using substantially standard CMOS frontend processing techniques, backend structures of the control circuit and the gas sensing structures (e.g., the MTJ element and the gas sensing element) are formed in the back end stack using minimally modified CMOS backend processing techniques, and then cavities are etched through the silicon substrate such that the gas sensing structures are disposed on thermally isolated "hot-plate" membrane structures. Gas sensors of the first novel arrangement utilizing any one or more of the various features mentioned above According to another novel sensor arrangement, a semiconductor gas sensor includes multiple MTJ elements that are operably coupled to a gas sensing element such that, similar to the first novel arrangement mentioned above, each MTJ element switches its resistance state in response to an ambient concentration level of a target gas in an environment containing the sensor, but in the second novel arrangement each MTJ element is caused to switch its resistance state at a target gas concentration level that is different from that of the other MTJ element(s) in order to provide more accurate quantitative gas concentration level information. For example, in a hypothetical two-element sensor embodiment, the gas sensing element would be operably coupled to the two MTJ elements that are respectively configured to switch resistance states at relatively low and relatively high gas concentration levels (e.g., such that the resistance state one of the MTJ elements switches from a low resistance value to a high resistance value only if currently measured gas concentration level is above the relatively low gas concentration level, and the other MTJ element switches from the initial to opposite resistance states only if the currently measured gas concentration level is above the higher gas concentration level). Using this novel sensor arrangement, the present invention facilitates accurate quantitative gas measurement by way of narrowing an actual (i.e., currently measured) gas concentration level to one of the ranges between the different (lower/higher) switching concentration levels at which the multiple MTJ elements switch resistance states. For example, using the two-MTJ-element example established above, an actual concentration level would be identified as falling into the range between zero gas concentration and the lower concentration level by way of determining that neither MTJ element switched resistance states during a corresponding exemplary gas sensing phase, as falling into the range between the lower and higher concentration levels by way of determining that only one of the two MTJ elements switched resistance states during a corresponding exemplary gas sensing phase, and as falling into a range above the higher concentration level by way of determining that both MTJ elements switched resistance states during a corresponding exemplary gas sensing phase. Note that varying (increasing or decreasing) the number of MTJ elements that switch resistance states at a different gas concentration levels varies the corresponding gas concentration measurement accuracy by way of varying (narrowing or widening) the ranges into which measured gas concentration levels fall, whereby gas sensors produced in accordance with second novel sensor approach are scalable to provide different measurement accuracies.

According to a preferred embodiment, gas sensors utilizing the multiple-MTJ sensor arrangement mentioned above include a "shared" field line structure that is operably magnetically coupled to all of the MTJ elements such that, when actuated during a gas sensing or reset phase, the shared field line structure generates a magnetic field that simultaneously applies a common magnetic orientation bias to all of the MTJ elements. For example, during an exemplary reset phase, the shared field line structure is actuated to generate a first magnetic field that biases all of the storage layers of the multiple MTJ elements into parallel directions relative to their associated reference layers. Because any number of MTJ elements can be controlled using the shared field line, gas sensors of the present invention implementing this shared field line approach are scalable to include any number of MTJ elements without requiring additional signal lines or other modifications to the control circuitry, thereby facilitating scalable quantitative gas concentration measurement resolution without increasing operating complexity.

According to alternative embodiments of the present invention, the multiple MTJ element approach mentioned above is utilized to produce either chemical-reaction-type semiconductor gas sensors or thermal-reaction-type semiconductor gas sensors. In the case of chemical-reaction-type gas sensors, the MTJ elements are operably physically coupled to a chemical-reaction-type gas sensing element in a manner consistent with conventional approaches such that changes in the composition or chemical structure of the gas sensing element in response to adsorption of sufficient target gas causes the MTJ elements to switch their resistance state. In this case, the MTJ elements are initialized into a reset magnetic orientation using conventional methods (e.g., heating to desorb gas while applying an external field), and the gas sensor is modified to cause switching at different target gas concentration levels during the subsequent gas sensing phase, for example, by way of implementing different MTJ size and shape effects (e.g., different thicknesses of the layers in the AFM/FM stack, different grain sizes in polycrystalline AFM and FM materials, different lateral sizes of the MTJ elements, etc.). In the case of thermal-reaction-type gas sensors, each MTJ element is produced with a different storage blocking temperature such that, as reaction heat generated by the thermal-reaction-type gas sensing element increases the temperatures of all of the MTJ elements at the same rate, switching of any given MTJ element occurs only when its temperature increases above its storage blocking temperature, which, as described above, occurs when the actual (currently measured) gas concentration level is at least equal to a switching concentration level needed to increase the given MTJ element's temperature to its storage blocking temperature. In some embodiments, the MTJ elements are intentionally provided with different storage blocking temperatures by way of controlling the fabrication process to produce each MTJ element with a different lateral size or a different AFM layer thickness. In other embodiments, the MTJ elements are generated using the same processing parameters (e.g., same lateral width and thickness), and the inherent blocking temperature distribution, which is typically in the range of 50-100° C., mostly due to fluctuations of the grain sizes in the AFM layers, is utilized to provide the desired different storage blocking temperatures. In a preferred embodiment, the thermal-reaction-type gas sensors utilizes a resistive heating element in the manner described above to generate optimal temperatures during the reset and gas sensing phases, and utilizes a shared field line to generate external magnetic fields utilized during the reset and/or gas sensing phases. By way of the above practical examples, those skilled in the art will recognize that the multiple MTJ element gas sensing approach described herein may be utilized with many different gas sensing technologies.

According to another embodiment of the present invention, the multiple MTJ element approach mentioned above is modified to includes multiple MTJ elements disposed in one or more NAND-type series-connected strings such that a total string resistance of each series-connected string is collectively defined by (i.e., substantially equal to a sum of) the corresponding MTJ resistances of the series-connected MTJ elements connected in the string. In this case, the gas sensor is configured to measure a target gas concentration level by way of generating a read current that passes through all of the series-connected MTJ elements forming the series-connected string, and determine the resistance states of the individual MTJ elements by way of determining the total string resistance (e.g., by measuring the read current). In an exemplary embodiment, the total string resistance of the series-connected string is initially set in a low resistance value by fixing all of the MTJ elements into the low resistance value during the reset phase, whereby the subsequent changes to the resistance state of one or more MTJ elements during the gas sensing phase is determined by the corresponding change in the total string resistance. With this arrangement, the gas sensor of the present invention facilitates determining an actual gas concentration level by determining the number of MTJ elements that switched resistance values during the gas sensing phase, then correlating the determined number of switched MTJ elements with previously measured gas concentration levels corresponding to the determined number of switched MTJ elements. In addition to providing a gas sensor capable of quantitative gas concentration level measurements by way of utilizing multiple MTJ elements that switch resistance values at different gas concentration levels, the NAND-type series-connected string arrangement further simplifies gas sensor control circuitry by way minimizing the number of read current measurements required to determine the resistance states of all of the MTJ elements. Further, gas sensors implementing the NAND-type series-connected string arrangement are readily scalable to provide a range of measurement accuracies, for example, by way of increasing the number of MTJ elements in each series-connected string or connecting multiple series strings in parallel, and/or by configuring each MTJ element of a series connected string to switch its resistance value at a slightly different gas concentration level, thereby providing gas sensors capable of measuring very small gas concentration level variations. Moreover, by combining the string approach with one or more of the approaches discussed above (e.g., by utilizing the inherent blocking temperature distribution to generate different blocking temperatures), low-cost semiconductor gas sensors capable of simultaneously quantitatively measuring several ambient gases (e.g., by way of forming separate strings including different sized MTJ elements on separate membranes). Moreover, because the MTJ elements' post-sensing resistance value is stored in a stable (i.e., non-volatile) state after the gas sensing phase, readout of the total string resistance is preferably performed after the MTJ elements have cooled to a low (e.g., room temperature), whereby thermal-reaction-type gas sensors implementing the NAND-type series-connected string arrangement achieve substantially higher readout accuracies in comparison to conventional thermal-reaction-type gas sensors that require measuring currents/resistances using MOSFETs during the gas sensing phase.

BRIEF DESCRIPTION OF THE DRAWINGS

These and other features, aspects and advantages of the present invention will become better understood with regard to the following description, appended claims, and accompanying drawings, where:

DETAILED DESCRIPTION OF THE DRAWINGS

The present invention relates to an improvement in semiconductor gas sensors utilized to detect and measure selected target gases in an environment. The following description is presented to enable one of ordinary skill in the art to make and use the invention as provided in the context of a particular application and its requirements. As used herein, directional terms such as "upper" and "lower" are intended to provide relative positions for purposes of description, and are not intended to designate an absolute frame of reference. In addition, the terms "coupled" and "connected", which are utilized herein, are defined as follows. The term "connected" is used to describe a direct connection between two circuit elements, for example, by way of a metal line formed in accordance with normal integrated circuit fabrication techniques. In contrast, the term "coupled" is used to describe either a direct connection or an indirect connection between two circuit elements. For example, two coupled elements may be directly connected by way of a metal line, or indirectly connected by way of an intervening circuit element (e.g., a capacitor, resistor, inductor, or by way of the source/drain terminals of a transistor). Various modifications to the preferred embodiment will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed.

Figure 1:
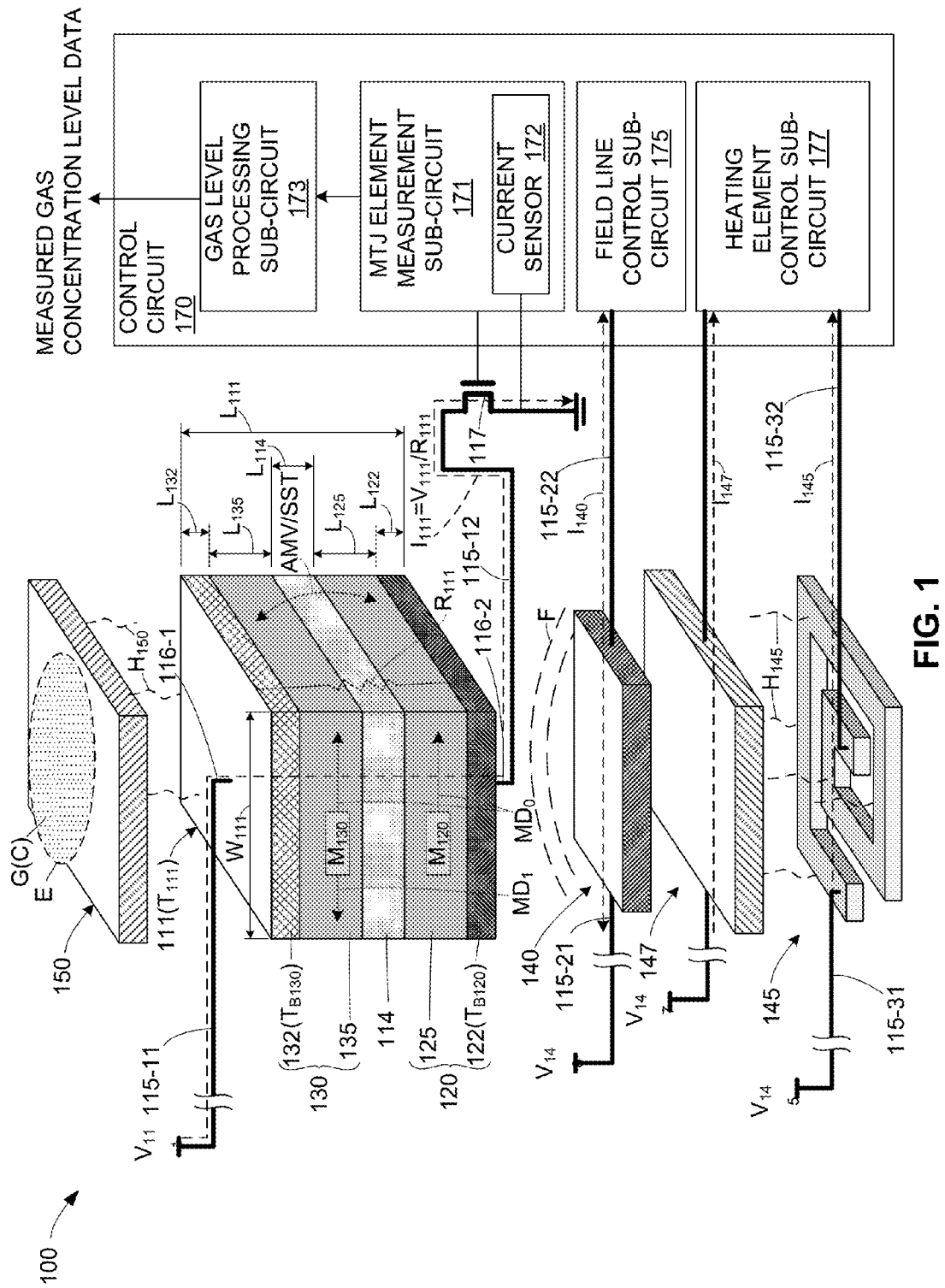
FIG. 1 is a simplified perspective view showing a semiconductor gas sensor including an MTJ element according to an embodiment of the present invention.

FIG. 1 shows a thermal-reaction-type gas sensor 100 for detecting a target gas G in an environment E according to a first exemplary embodiment of the present invention. Gas sensor 100 includes a magnetic tunnel junction (MTJ) element 111 that is operably thermally coupled to a gas sensing element 150 such that an MTJ temperature $T_{111}$ of MTJ element 111 is at least partially influenced by reaction heat $H_{150}$ generated by gas sensing element 150. Although not shown in FIG. 1, it is understood that an intervening structure (e.g., a layer of dielectric material) is disposed between gas sensing element 150 and MTJ element 111.

MTJ element 111 generally includes a reference layer 120 and a storage layer 130 separated by a tunnel dielectric layer 114. Reference layer 120 includes a magnetic structure that defines a reference magnetic orientation $M_{120}$, and storage layer 130 includes a second magnetic structure that defines a storage magnetic orientation $M_{130}$. According to an aspect of the present invention, reference layer 120 is configured as a high-coercivity magnetic structure such that reference magnetic orientation $M_{120}$ remains fixed in a single magnetic direction during normal operation of gas sensor 100, and storage layer 130 is configured as a low-coercivity magnetic structure such that storage magnetic orientation $M_{130}$ is switchable (changeable) between two magnetic directions during normal operation of gas sensor 100, whereby a resistance state $R_{111}$ of MTJ element 111 is changeable (switchable) between two (i.e., relatively low and relatively high) resistance values. In the exemplary embodiment, reference layer 120 is configured such that reference magnetic direction $M_{120}$ remains fixed in first magnetic direction $MD_0$, which is depicted using right-pointing arrow in FIG. 1, and storage layer 130 is configured such that storage magnetic orientation $M_{130}$ is switchable between first magnetic direction $MD_0$ and second magnetic direction $MD_1$, which is depicted using left-pointing arrow in FIG. 1 (i.e., opposite to magnetic direction $MD_0$). The magnetic orientations of reference layer 120 and storage layer 130 are "parallel" when storage magnetic orientation $M_{130}$ is fixed in the same direction as reference magnetic direction $M_{120}$ (e.g., both storage magnetic orientation $M_{130}$ and reference magnetic direction $M_{120}$ are aligned in first magnetic direction $MD_0$). Conversely, the magnetic orientations of reference layer 120 and storage layer 130 are "anti-parallel" when storage magnetic orientation $M_{130}$ is fixed in an opposite direction to that of reference magnetic direction $M_{120}$ (e.g., storage magnetic orientation $M_{130}$ is fixed in second magnetic direction $MD_1$ and reference magnetic direction $M_{120}$ is fixed in first magnetic direction $MD_0$). A current resistance state $R_{111}$ of MTJ element 111 is correlated to the parallel/non-parallel directions in that resistance state $R_{111}$ has a low resistance value when storage magnetic orientation $M_{130}$ is parallel to reference magnetic orientation $M_{120}$, and has a high resistance value when storage magnetic orientation $M_{130}$ is anti-parallel/opposite to reference magnetic orientation $M_{120}$. For reference, typical resistances of high and low states for an MTJ having a diameter of 200 nm and MgO thickness of 12-14 Å are 2 kOhm and 700 Ohm to 1 kOhm, respectively, which corresponds to a tunnel magneto-resistance ratio (TMR) of approximately 100% to 200%. Accordingly, the parallel/antiparallel orientation of storage layer 130 relative to reference layer 120 at a given point in time can be easily determined by way of determining resistance state $R_{111}$ of MTJ element 111 at that time.

According to an aspect of the first exemplary embodiment, storage magnetic orientation $M_{130}$ is made switchable between parallel and anti-parallel directions relative to reference magnetic orientation $M_{120}$ by way of configuring storage layer 130 such that its associated storage blocking temperature $T_{B130}$ that is within the normal operating temperature range experienced by MTJ element 111 (i.e., the temperature range of MTJ temperature $T_{111}$), and by way of configuring reference layer 120 such that it has an associated reference blocking temperature $T_{B120}$ that is higher than the normal operating temperature range experienced by MTJ element 111. The normal operating temperature range of MTJ temperature $T_{111}$ is established by temperatures generated on gas sensor 100 under normal operating conditions, whereby MTJ temperature $T_{111}$ of MTJ element 111 normally varies between a minimum temperature (e.g., room temperature, approximately 24° C.) and a maximum temperature (e.g., approximately 250° C.). In one embodiment, storage layer 130 is a multi-layer structure including an antiferromagnetic (AF) structure 132 and a ferromagnetic structure 135 disposed in close proximity such that an exchange interaction between the two structures produces storage magnetic direction $M_{130}$, and the desired switchability of storage magnetic orientation $M_{120}$ at normal operating temperatures of gas sensor 100 is achieved by way of fabricating AF structure 132 using an AF material having an associated storage blocking temperature $T_{B130}$ that is within the expected normal operating temperature range of MTJ temperature $T_{111}$. That is, when a temperature of AF structure 132 is below its associated storage blocking temperature $T_{B130}$, it becomes highly resistant to switching its magnetic direction in response to an external magnetic bias force, whereby storage magnetic direction $M_{130}$ becomes "fixed" (i.e., pinned or unchangeable) in one of two directions (e.g., $MD_0$ or $MD_1$). Conversely, when the temperature of AF structure 132 is above its associated storage blocking temperature $T_{B130}$, AF structure 132 becomes less resistant to change, whereby storage magnetic orientation $M_{130}$ is switchable between directions $MD_0$ and $MD_1$ by applied magnetic bias forces (e.g., external magnetic fields). With storage layer 130 configured in this way, storage magnetic orientation $M_{130}$ is switchable during operation of gas sensor 100 whenever MTJ temperature $T_{111}$ increases above storage blocking temperature $T_{B130}$. In contrast, reference layer 120 is fabricated using a different AF structure 122 disposed in contact with an associated ferromagnetic structure 125, where AF structure 122 is fabricated using an AF material having an associated storage blocking temperature $T_{B120}$ that is greater than the normal operating temperature range of MTJ element 111, whereby reference magnetic orientation $M_{120}$ remains permanently fixed (e.g., in first magnetic direction $MD_0$) because MTJ temperature $T_{111}$ of MTJ element 111 does not increase above reference blocking temperature $T_{B120}$ during normal operations of gas sensor 100.

According to a presently preferred embodiment illustrated in FIG. 1, MTJ element 111 is produced in a stack-type arrangement with (first) ferromagnetic structure 125 and (second) ferromagnetic structure 135 respectively disposed in contact with opposite (upper and lower) surfaces of tunnel dielectric layer 114, and with (first) AF structure 122 and (second) AF structure 132 respectively disposed on respective opposite (upper and lower) surfaces of ferromagnetic structures 125 and 135. In a specific exemplary embodiment, ferromagnetic layers 125 and 135 comprise one or more of Fe, Co, Ni and their alloys, such as, e.g., FeCo. According to an aspect of the preferred embodiment, reference AF structure 122 comprises a first AF material exhibiting associated reference blocking temperature $T_{B120}$ and storage AF structure 132 comprises a second (different) AF material having associated storage blocking temperature $T_{B130}$, where the two different AF materials are selected such that the reference blocking temperature $T_{B120}$ is substantially greater (higher) than the storage blocking temperature $T_{B130}$. More specifically, reference AF structure 122 comprises a first AF material having a reference blocking temperature $T_{B120}$ that is preferably higher than the maximum expected operating temperature of gas sensor 100 (e.g., greater than approximately 250° C.), whereby reference magnetic orientation $M_{120}$ remains effectively permanently fixed (e.g., in direction $MD_0$ indicated in FIG. 1) after being initialized during fabrication. In contrast, storage AF structure 132 comprises an AF material having a storage blocking temperature $T_{B130}$ that is approximately midway within the expected normal operating temperature range of gas sensor 100 (e.g., approximately 125° C.). In a specific exemplary embodiment, reference AF structure 122 comprises an AF material (e.g., one or more of PtMn or NiMn) having a reference blocking temperature $T_{B120}$ in the range of 250-350° C., and storage AF structure 132 comprises an AF material (e.g., one or more of FeMn or IrMn) having a storage blocking temperature $T_{B130}$ in the range of 120-250° C. In one embodiment, the AF material in each layer can be coupled to a synthetic AF structure comprising of two magnetic layers sandwiched with a thin ruthenium layer—such a synthetic AF structure has a very strong antiparallel coupling. If the ferromagnetic with AF pinning is coupled also to a synthetic AF structure, the coupling of the reference ferromagnetic layer over the storage ferromagnetic layer is small (synthetic AF structures produce small stray magnetic fields extending into the opposite electrode).

In an exemplary embodiment (referring to FIG. 1), MTJ element 111 has an overall cell thickness $L_{111}$ in the range of 50 to 200 nanometers, and has a nominal width/diameter $W_{111}$ (i.e., maximum top view dimension) in the range of 50 to 500 nanometers, and more preferably in the range of 100 to 250 nanometers. Reference AF structure 122 is fabricated with a thickness $L_{122}$ in the range of 10 and 30 nm, reference ferromagnetic structure 125 is fabricated with a thickness $L_{125}$ in the range of 5 and 70 nm, tunnel dielectric layer 114 (e.g., magnesium oxide (MgO) or aluminum oxide ($Al_2O_3$)) is fabricated with a thicknesses $L_{114}$ in the range of 10 to 20 Angstroms, storage ferromagnetic structure 135 is fabricated with a thickness $L_{135}$ in the range of 5 and 70 nm, and storage AF structure 132 is fabricated with a thickness $L_{132}$ in the range of 5 and 30 nm. Forming MTJ element 111 using these dimensions both minimize fabrication defects (e.g., shorts) and produces desirable resistance characteristics that facilitate the write/program and compare operations that are described below.

In one embodiment, MTJ element 111 is further configured such that an anti-parallel alignment of magnetization vectors (AMV) force or spin torque transfer STT (spin-polarized current) is directed from reference layer 120 into the free magnetic layer (storage layer 130) with sufficient magnetic force to facilitate switching of storage magnetic orientation $M_{130}$ during the operating cycle of gas sensor 100. In the case of AMV, although magnetic fields typically do not extend outside each AFM/FM stack, it is possible to modify layer borders and grains of the AFM such that a magnetic field generated by reference layer 120 imposes a magnetic bias on storage layer 120 having sufficient strength to switch storage layer 120 from the parallel to the anti-parallel orientation. In the case of spin torque transfer (STT), an electrical current in the MTJ causes spin torque that is transferred by electrons moving from reference layer 120 to storage layer. Referring to FIG. 1, both force AMV and spin torque STT are directed from reference layer 120 to storage layer 130, where a magnetic moment (indicated by the double-headed dashed-line arrow in FIG. 1) is transferred to storage layer 130 by the bias force or spin torque of electrons polarized by reference layer 120. Both the AMV force and spin torque transfer result in bias forces similar to the repelling force experienced by two bar magnets placed in parallel with their North poles together—in the absence of a countering force, one of the magnets will rotate because a North-to-South pole alignment is the lower energy state. When the dimensions of MTJ element 111 are adjusted using known techniques to sufficiently enhance AMV, the resulting field provides a sufficiently strong magnetic bias force that can be used to bias storage magnetic orientation $M_{130}$ into the anti-parallel direction relative to reference magnetic orientation $M_{120}$ when MTJ temperature $T_{111}$ is above storage blocking temperature $T_{B130}$ (i.e., and below reference blocking temperature $T_{B120}$, and in the absence of a conflicting external magnetic biasing field). Specifically, when storage magnetic orientation $M_{130}$ and reference magnetic orientation $M_{120}$ are in parallel directions (e.g., referring to FIG. 1, both are fixed in first magnetic direction $MD_0$) and then MTJ temperature $T_{111}$ is increased above storage blocking temperature $T_{B130}$ (and no current is supplied to field line structure 140), force AMV causes storage magnetic orientation $M_{130}$ to switch to the anti-parallel (opposite) direction relative to reference magnetic orientation $M_{120}$ (i.e., such that reference magnetic orientation $M_{120}$ remains fixed in first magnetic direction $MD_0$, but storage magnetic orientation M130 switches to second magnetic direction $MD_1$). Configuring MTJ element 110 to produce sufficient AMV force therefore provides an advantage over STT and field line force F2 in that this arrangement facilitates reliably switching resistance state $R_{111}$ of MTJ element 111 from the low resistance (parallel direction) value to the high resistance (anti-parallel direction) value without applying any current to gas sensor 100, thereby facilitating low energy consumption operations.

Referring again to FIG. 1, gas sensing element 150 is disposed on an external region of gas sensor 100 such that it physically contacts environment E (and, hence, target gas G, when present in environment E) during gas sensing operations, and is disposed relative to MTJ element 111 such that reaction heat $H_{150}$ generated by gas sensing layer 150 significantly influences MTJ temperature $T_{111}$ of MTJ element 111. In one embodiment, gas sensing element 150 is separated from by a thin layer of passivation material (not shown), and is configured in a manner similar to thermal-reaction-type gas sensing elements used in conventional thermal-reaction-type gas sensors such that reaction heat $H_{150}$ is generated by gas sensing element 150 in an amount proportion to an actual (currently measured) concentration level C of target gas G in environment E. In a presently preferred embodiment, gas sensing element 150 is a combustion-type gas sensing element in which reaction heat $H_{150}$ is generated by combustion of target gas G that comes into contact with gas sensing element 150 in a manner consistent with conventional reaction type (ii), which is described in the background section above. In an alternative embodiment, gas sensing element 150 is implemented using reaction type (iii) in which reaction heat $H_{150}$ is produced by way of thermal conductivity of target gas G passing over gas sensing element 150.

According to another aspect of the first embodiment, gas sensor 100 is configured such that reaction heat $H_{150}$ generated by gas sensing element 150 during a gas sensing phase increases MTJ temperature $T_{111}$ of MTJ element 111 from a lower temperature above (i.e., equal to or greater than) storage blocking temperature $T_{B130}$ only when currently measured concentration level C of target gas G in environment E is above (i.e., equal to or greater than) a predetermined minimum concentration level. That is, because the amount of reaction heat $H_{150}$ generated by gas sensing element 150 is proportional to a given measured concentration level, because MTJ temperature $T_{111}$ of MTJ element 111 is proportional to reaction heat $H_{150}$ by way of the operable thermal coupling between gas sensing element 150 and MTJ element 111, and because storage magnetic orientation $M_{130}$ resists switching directions (i.e., from parallel to anti-parallel directions, or vice versa) unless MTJ temperature $T_{111}$ is above storage blocking temperature $T_{B130}$, gas sensor 100 is configured to indicate whether a currently measured concentration level C of target gas G is above or below the predetermined minimum gas concentration level by way of the switched/non-switched state of storage layer 130 after the gas sensing phase. For example, when a given measured concentration level C of target gas G were below the predetermined minimum concentration level, the generated amount of reaction heat $H_{150}$ would be insufficient to increase MTJ temperature $T_{111}$ above storage blocking temperature $T_{B130}$, whereby switching of storage magnetic orientation $M_{130}$ would not be possible, and gas sensor 100 would indicate that the given measured concentration level is below the predetermined minimum gas concentration level by way of the non-switched state of storage layer 130 after completion of the gas sensing phase. Conversely, when a given measured concentration level C of target gas G is above the predetermined minimum concentration level, the generated amount of reaction heat $H_{150}$ increases MTJ temperature $T_{111}$ above storage blocking temperature $T_{B130}$, whereby switching of storage magnetic orientation $M_{130}$ is made possible (i.e., by way of an applied magnetic bias force, as described below), and gas sensor 100 indicates that the given measured concentration level is above the predetermined minimum gas concentration level by way of the resulting switched state of storage layer 130 after completion of the gas sensing phase. Thus, by configuring gas sensor 100 such that reaction heat $H_{150}$ increases MTJ temperature $T_{111}$ above storage blocking temperature $T_{B130}$ only when currently measured concentration level C is above the predetermined minimum concentration level, the present invention facilitates detecting target gas G in concentration levels above the predetermined minimum gas concentration level by way of determining the switched/non-switched state of storage magnetic orientation $M_{130}$ after a given gas sensing phase of the gas sensor's operating cycle.

According to an exemplary specific embodiment depicted in simplified form in FIG. 1, the readout of resistance state $R_{111}$ of MTJ element 111 is implemented by coupling MTJ element 111 between a read voltage source $V_{111}$ and a ground terminal by way of a select transistor 117, and controlling select transistor 117 by way of MTJ element measurement sub-circuit 171 during the readout phase (and, optionally, at the end of the reset phase) of each sensor operating cycle. More specifically, voltage source $V_{111}$ is applied on a conductive line 115-11 (e.g., metallization line), which is coupled to storage AF layer 132 of MTJ element 111 by way of a metal via 116-1, and reference AF layer 122 of MTJ element 111 is in turn connected by way of a metal via 116-2 and a conductive line 115-12 to ground by way of select transistor 117. With this arrangement, determining resistance state $R_{111}$ of MTJ element 111 is achieved by turning on select transistor 117 to generate a read current $I_{111}$ from fixed voltage source $V_{111}$ through MTJ element 111, measuring the resulting read current $I_{111}$ (e.g., using a current sensor 172), and the determining the high/low resistance value of resistance state $R_{111}$ by way of determining whether read current is relatively high (indicating resistance state $R_{111}$ is low) or relatively low (indicating resistance state $R_{111}$ is high).

Referring again to FIG. 1, gas sensor 100 further includes an on-chip field line structure 140 that is physically spaced from MTJ element 111 by an intervening dielectric or insulating structure (not shown), is operably magnetically coupled to storage layer 130 of MTJ element 111, and is configured to generate an external magnetic field F exerting a magnetic force that allows external magnetic field F to serve as the magnetic biasing force utilized to reset and/or switch storage magnetic orientation $M_{130}$ during reset and/or read operating phases. In the disclosed embodiment, field line structure 140 comprises an elongated metal structure that is coupled to a voltage source $V_{140}$ by a conductor 115-21 and to a field line control sub-circuit 175 by way of a conductor 115-22, and field line sub-circuit 175 is configured to actuate field line structure 140 to generate field F by way of generating a field line current $I_{140}$ through field line structure 140, whereby a magnetic direction of the magnetic field F is changeable by way of changing the flow direction of field line current $I_{140}$. As described in additional detail below, this arrangement facilitates switching storage magnetic orientation $M_{130}$ between the parallel and anti-parallel directions relative to reference magnetic orientation $M_{120}$ when MTJ temperature $T_{111}$ is above storage blocking temperature $T_{B130}$, and may be used in either or both of the reset and readout phases of the sensor operating cycle. Although on-chip field line 140 may be required for the operations of gas sensor 100 described below, in some embodiments (not shown) suitable alternative magnetic bias forces that are utilized during the reset and/or gas sensing phases may be generated from off-chip sources, and in such embodiments field line 140 may be omitted.

Referring to the lower left portion of FIG. 1, according to another embodiment, gas sensor 100 further includes an on-chip resistive heating element 145 that is physically spaced from field line structure 140 by an intervening dielectric or insulating structure (not shown), is operably thermally coupled to MTJ element 111 and to gas sensing element 150, and is configured to generate control heat $H_{145}$. In the disclosed embodiment, heating element 145 comprises a coil structure that is formed using polycrystalline silicon or Tungsten that is coupled to a voltage source $V_{145}$ by a conductor 115-31 and to a heating element control sub-circuit 177 by way of a conductor 115-32, and heating element control sub-circuit 177 is configured to actuate heating element 145 by way of generating a heater current $I_{145}$ from voltage source $V_{145}$ through heating element 145. As set forth below, heating element control sub-circuit 177 is configured to actuate heating element 145 during the reset and readout operating phases such that control heat $H_{145}$ increases/decreases the temperatures of MTJ element 111 and gas sensing element 150 to create desired operating temperatures on gas sensor 100. In one embodiment, the actuation of heating element 145 is controlled using a temperature sensor 147 that is coupled between a voltage source $V_{147}$ and heating element control sub-circuit 177, and is configured using known techniques such that a temperature sensor control current $I_{147}$ passing through temperature sensor 147 provides heating element control sub-circuit 177 with real-time temperature data usable for controlling heating element 145 to generate the desired operating temperatures. Although on-chip heating element 145 may be required for the operations of gas sensor 100 described below, in some embodiments (not shown) the required control heat may be generated from off-chip heat sources, and in such embodiments heating element 145 may be omitted.

Figure 2:
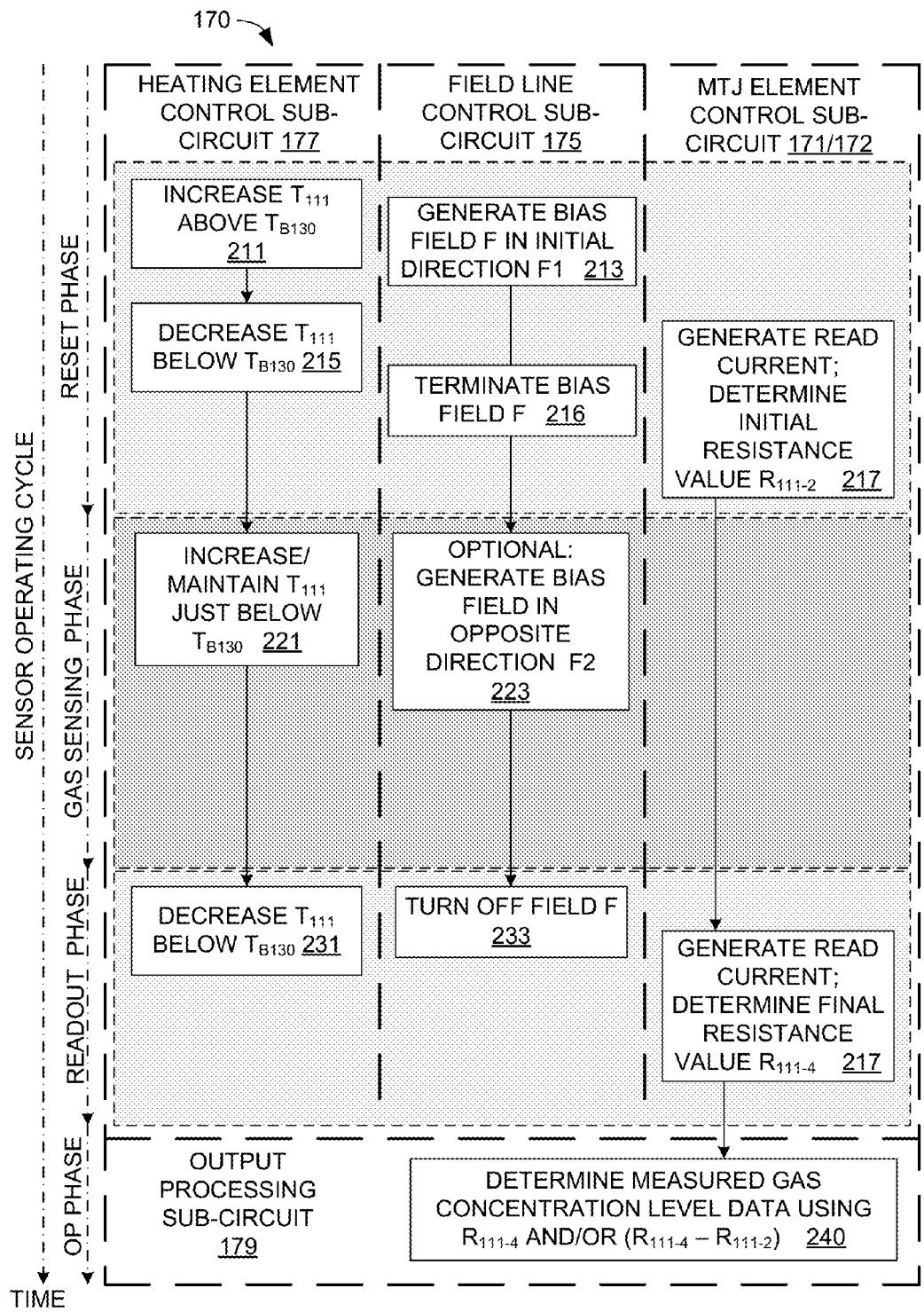
FIG. 2 is flow diagram showing an exemplary operating cycle performed by the gas sensor of FIG. 1 according to another embodiment of the present invention.
Figure 3A:
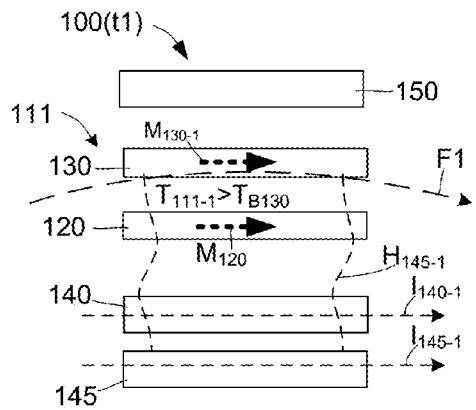
FIGS. 3(A), 3(B), 3(C), 3(D), 3(E) and 3(F) are simplified side views showing the gas sensor of FIG. 1 during various operating phases of the operating cycle shown in FIG. 2.
Figure 3B:
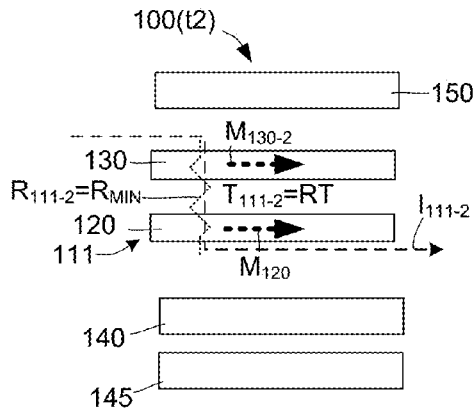
Figure 3C:
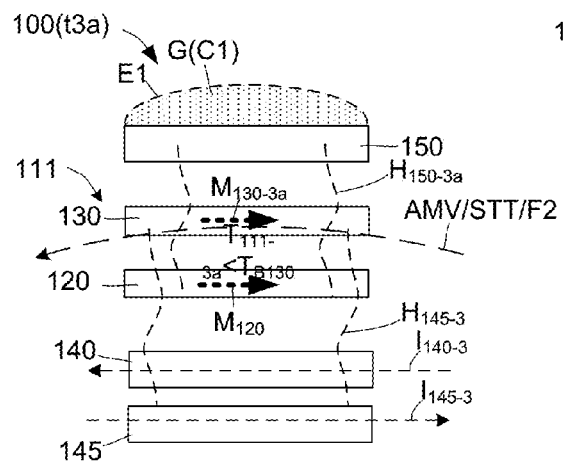
Figure 3D:
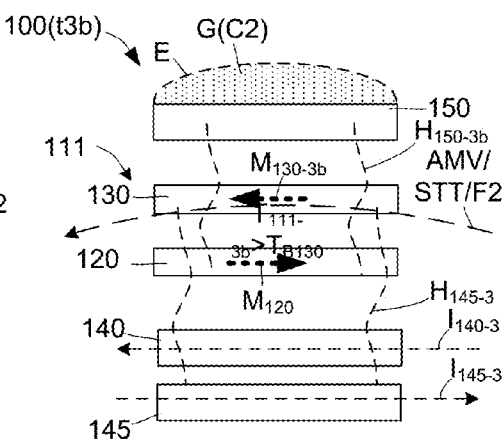

FIG. 2 is a flow diagram depicting an exemplary sensor operating cycle implemented by gas sensor 100 (FIG. 1) during normal operating conditions according to another embodiment of the present invention. As indicated along the left edge of FIG. 2, the sensor operating cycle is generally divided into a reset phase, a gas sensing phase, a readout phase, and an optional output processing (OP) phase that are performed sequentially as indicated by the TIME arrow located along the left edge of FIG. 2. Also included in FIG. 2 are references to the various sub-circuits of control circuit 170 (FIG. 1) that function as described below during the various phases of the operating cycle. In addition, exemplary operation cycle phases are described with reference to FIG. 2 are depicted with reference to gas sensor 100 in a simplified form in FIGS. 3(A) through 3(F), wherein the notation "t[xy]" next to the reference number "100" denotes relative time and alternative operating conditions. For example, FIG. 3(A) depicts gas sensor 100 at an initial time t1, which is indicated by the notation "100(*t*1)", and FIGS. 3(C) and 3(D) depict gas sensor 100 at a subsequent time t3 under two different operating conditions, which are indicated by the notations "100(*t*3*a*)" and "100(*t*3*b*)". Similarly, various signals and magnetic orientations include the time-indicating suffix "-x" indicating a state of the signal/orientation at the associated time period (e.g., MTJ temperature $T_{111\text{-}1}$ in FIG. 3(A) denotes MTJ temperature $T_{111}$ at time t1). The time sequence notation is intended merely to denote the relative operation sequence, and is not intended to denote a uniform time period between each depicted operation process. Note that, as described below, the present invention is preferably implemented using multiple series-connected MTJ elements in order to produce high resolution quantitative gas concentration level information. As such, although the sensor operating cycle depicted in FIG. 2 is described in a simplified form with reference to single-MTJ-element gas sensor 100, the methodology set forth in FIG. 2 is understood to also apply to gas sensors utilizing multiple series-connected MTJ elements.

Referring to the upper left portion of FIG. 2, the sensor operating cycle begins with the reset phase, which functions to initialize (fix) the resistance state of MTJ element 111 in an initial (first) resistance value. Note that the exemplary embodiment implements a low initial resistance state (i.e., parallel magnetic orientation between the reference and storage layers) to facilitate using AMV or STT to cause switching during the subsequent gas sensing phase, which is preferred for reasons set forth below, but an initial high resistance state (i.e., anti-parallel magnetic orientation) may also be used, but this would require an applied external field to generate switching during the gas sensing phase.

Referring to the upper left portion of FIG. 2, the reset phase includes increasing MTJ temperature $T_{111}$ above storage blocking temperature $T_{B130}$ (block 211), applying a magnetic bias force having the desired initial magnetic direction (block 213), then decreasing MTJ temperature $T_{111}$ below storage blocking temperature $T_{B130}$ (block 215). This three-stage process for fixing storage magnetic orientation $M_{130}$ in the desired initial (parallel) direction may be accomplished using various techniques. In the exemplary (and presently preferred) embodiment indicated in FIG. 2, the heating/cooling processes (blocks 211 and 215) are positioned under the heading HEATING ELEMENT CONTROL SUB-CIRCUIT 177 to indicate that these processes are implemented by heating element 145 of gas sensor 100 (FIG. 1), and the applied bias force process (block 213) is positioned under the heading FIELD LINE CONTROL SUB-CIRCUIT 175 to indicate that the applied bias force is generated by field line structure 140 of gas sensor 100 (FIG. 1). As indicated in FIG. 3(A), the required control heat $H_{145-1}$ is generated by activating heating element 145 using an applied heater current $I_{145-1}$, and the required magnetic bias force is generated by applying a field line current $I_{140-1}$ to field line structure 140 such that it generates a (first) external magnetic field F1 having the desired magnetic direction (indicated by the curved dashed-line arrow pointing left in FIG. 3(A)). Subsequent cooling of MTJ element 111 below storage blocking temperature $T_{B130}$ is implemented in the exemplary embodiment by de-activating heating element 145 (i.e., terminating heater current $I_{145-1}$), whereby heat transfer from MTJ element 111 to adjacent cooler structures causes MTJ temperature $T_{111}$ to decrease. In alternative embodiments (not shown), other heat sources (e.g., adjacent MTJ elements) may be utilized to generate the required heat energy, and the cooling process may be enhanced, by way of heat sink structures. Moreover, applying the required magnetic bias force may be implemented using other structures and/or applied in a direction opposite to the exemplary (parallel) direction. For example, a spin torque transfer generated by reference layer 120 may be used to fix storage magnetic orientation $M_{130}$ in an initial anti-parallel direction relative to reference magnetic orientation $M_{120}$. In view of these options, it is understood the appended claims are not limited to the exemplary embodiment unless otherwise specified.

After the storage magnetic orientation is fixed in its initial direction (i.e., after MTJ temperature $T_{111-1}$ falls below storage blocking temperature $T_{B130}$ per block 215), the initial magnetic bias force used to set storage magnetic orientation $M_{130}$ in the initial direction is no longer needed. Referring again to the central column of FIG. 2, because this initial magnetic bias force is generated by way of activating the field line structure to generate external magnetic field F (block 213), terminating the magnetic bias force is implemented by de-activating the field line structure, which is depicted in FIG. 3(B) by way of the absence of a field line current applied to field line structure 140. In the case where spin torque transfer is used to reset the storage magnetic orientation, terminating this force is not possible, so the terminate process of block 216 is considered optional.

Referring block 217 on the right side of FIG. 2, in one embodiment an initial resistance value $R_{111-2}$ of MTJ element 111 is determined at the end of the reset phase to facilitate correlated double sampling (CDS) readout operations. Note that block 217 is located under the heading MTJ ELEMENT CONTROL SUB-CIRCUIT 171/172 to indicate that this process is implemented by way of utilizing MTJ element measurement circuit 171 and current sensor 172 (both shown in FIG. 1 and described above). FIG. 3(B) depicts gas sensor 100($t2$) during an exemplary initial readout process during which MTJ element 111 is coupled to a fixed read voltage (i.e., $V_{111}$, shown in FIG. 1), and the resulting read current $I_{111-2}$ passing through MTJ element 111 is measured that indicates initial resistance $R_{111-1}$. Note that, because storage magnetic orientation $M_{130-2}$ remains fixed in the initial parallel direction relative to reference magnetic orientation $M_{120}$, initial resistance $R_{111-1}$ of MTJ element 111 has a relatively low resistance value (indicated as "$R_{MIN}$" in FIG. 3(B)). In addition, according to a presently preferred embodiment, the initial readout process is conducted after MTJ element has cooled substantially to room temperature (indicated in FIG. 3(B) by "$T_{111-2}=RT$") before measuring read current $I_{111-2}$.

As indicated along the left side of FIG. 2, the gas sensing phase is performed at the end of the resent phase. The gas sensing phase generally involves maintaining MTJ element 111 at a temperature below storage blocking temperature $T_{B130}$ while applying a magnetic bias force corresponding to the anti-parallel direction of the reference and storage layer magnetizations in the MTJ element, where gas sensor 100 is configured such that the presence of target gas G above (i.e., equal to or greater than) a predetermined minimum concentration level will cause gas sensing element 150 to generate sufficient reaction heat $H_{150}$ to raise MTJ temperature $T_{111}$ above storage blocking temperature $T_{B130}$, thereby causing storage magnetic orientation $M_{130}$ to switch from the parallel to the anti-parallel direction. As discussed below, each of the two operating parameters required to affect the gas sensing phase (i.e., proper MTJ temperature and applied magnetic bias field) may be achieved by alternative methodologies, and as such the illustrated examples described below are not intended to be limiting.

Referring to FIG. 2 and to FIGS. 3(A) and 3(B), in the illustrated embodiment maintaining MTJ element 111 at a temperature slightly below storage blocking temperature $T_{B130}$ in the illustrated embodiment is achieved by actuating heating element 145 to generate control heat $H_{145-3}$ in an amount that increases (i.e., when starting from a lower temperature) and maintains MTJ temperature $T_{111-3}$ at an optimal predetermined gas sensing, which is referred to herein as a work point temperature. As explained in additional detail below with reference to FIG. 8, the work point temperature of a given sensor arrangement coincides with the lowest temperature at which reaction heat $H_{150-3}$ is generated by gas sensing element 150 in response to target gas G, and storage blocking temperature $T_{B130}$ of MTJ element 111 is set an amount above the work point temperature such that gas sensing element 150 generates an amount of reaction heat $H_{150-3}$ that increases MTJ temperature $T_{111-3}$ from the work point temperature to storage blocking temperature $T_{B130}$ when target gas G is present at the predetermined minimum concentration level. By way of illustrative example, FIGS. 3(C) and 3(D) show two gas alternative sensing phases, with gas sensor 100($t3a$) in FIG. 3(C) disposed in an environment E1 including target gas G at a relatively low gas concentration level C1, and gas sensor 100($t3b$) in FIG. 3(D) disposed in an environment E2 including target gas G at a relatively high gas concentration level C2. In both cases, heating element 145 receives the same heater current $I_{145-3}$ such that the same amount of control heat $H_{145-3}$ is generated in both FIGS. 3(C) and 3(D). In the case illustrated in FIG. 3(C), because currently measured gas concentration level C1 of target gas G is below the predetermined minimum gas concentration level, the combination of reaction heat $H_{150-4a}$ generated by gas sensing element 150 and control heat $H_{145-3}$ generated by heating element 145 fails to increase MTJ temperature $T_{111-3b}$ from the work point temperature to storage blocking temperature $T_{B130}$, whereby storage magnetic orientation $M_{130-3a}$ remains fixed (i.e., remains in the initial parallel direction relative to reference magnetic orientation $M_{120}$), and resistance state $R_{111}$ of MTJ element 111 retains its initial low resistance value. In contrast, as illustrated in FIG. 3(D), when currently measured gas concentration level C2 of target gas G is above the predetermined minimum gas concentration level, reaction heat $H_{150-4b}$ generated by gas sensing element 150 combines with control heat $H_{145-3}$ to increase MTJ temperature $T_{111-3b}$ from the work point temperature to a temperature above storage blocking temperature $T_{B30}$, thereby unpinning storage layer 130 such that magnetic bias force STT/F2 biases storage magnetic orientation $M_{130-3b}$ into the anti-parallel (second) direction relative to reference magnetic orientation $M_{120}$, whereby resistance state $R_{111}$ of MTJ element 111 switches from the initial low resistance value to a high resistance value. The work point temperature is generally determined by heating element 150 and the target gas type (i.e., for a given gas sensor, the work point temperature changes for different target gasses). Similarly, as discussed in additional detail herein, the storage blocking temperature $T_{B130}$ for a given MTJ element 111 is generally fixed (unchangeable) after fabrication, but may be influenced during fabrication by random factors (e.g., crystal grain size) and different design parameters (e.g., lateral size and layer thickness). Therefore, the predetermined gas concentration level for gas sensor 100 is the target gas concentration level at which heating element 150 generates the amount of reaction heat $H_{150}$ required to increase MTJ temperature $T_{111}$ from the work point temperature to storage blocking temperature $T_{B130}$, and therefore is adjustable either by way of altering heating element 150 (i.e., configuring heating element 150 such that the work point temperature is set at an optimal temperature for a given storage blocking temperature), or by altering MTJ element 111 (i.e., by configuring MTJ element 111 such that storage blocking temperature $T_{B130}$ occurs at an optimal temperature for a given work point temperature).

Although increasing/maintaining MTJ element 111 at the work point temperature involves actuating on-chip heater 145 in a preferred embodiment, achieving/maintaining the work point temperature may be achieved using other methods. For example, in cases where the work point temperature may be room temperature, no control heat would be needed to maintain MTJ element at room temperature. In other cases, an off-chip heat source may be used to maintain gas sensor 100 at the work point temperature. Accordingly, unless specified in the appended claims, maintaining MTJ element 111 at the work point temperature during the gas sensing phase should not be limited to generating control heat using an on-chip heating element such as heating element 145.

Turning to the applied magnetic bias force parameter that is required to perform the gas sensing phase, as illustrated in FIGS. 3(C) and 3(D), a benefit of initializing storage layer 130 in the low resistance state is that spin torque transfer STT (discussed above) or even no external magnetic field could be utilized to provide the applied magnetic bias force during the gas sensing phase. In the latter case, the exchange interaction of the reference and storage layers serves the function of the external magnetic force. MTJ elements are switched into the high resistance state (antiparallel orientations of storage and reference layer magnetizations) due to the magnetic interaction of the reference layer with the storage layer. This benefits gas sensing operation because it allows gas sensor 100 to perform gas sensing at zero operating voltages by way of eliminating the need for an externally generated magnetic bias force. Switching of the storage layer can be facilitated by using external magnetic fields at the stage of sensing (if the exchange bias from the reference is not sufficient to switch the storage layer). In this case, e.g. spin torque transfer can be used. Alternatively, as indicated by block 223 in FIG. 2 and in FIGS. 3(C) and 3(D), in the case where spin torque transfer is not available in sufficient strength to produce reliable switching, the magnetic bias force applied to MTJ element 111 during the gas sensing phase may be applied in the form of a (second) external magnetic field F2 generated by way of passing a field line current $I_{140-3}$ in a direction opposite to reset field line current $I_{140-1}$ (see FIG. 3(A)), whereby external magnetic field F2 biases storage layer 130 in the anti-parallel direction to facilitate switching of MTJ element 130 when the measured target gas concentration is above the predetermined minimum concentration level. In yet another embodiment, both spin torque transfer STT and external magnetic field F2 are utilized to produce a reliable magnetic bias force.

Figure 3E:
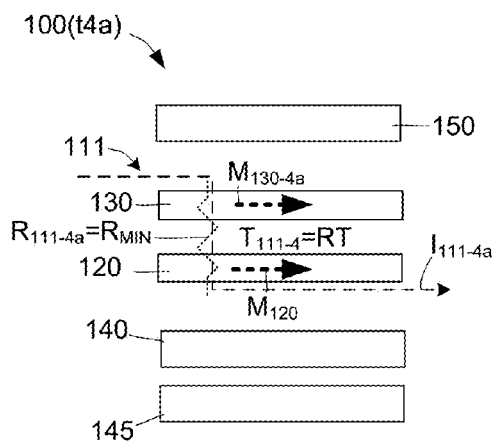
Figure 3F:
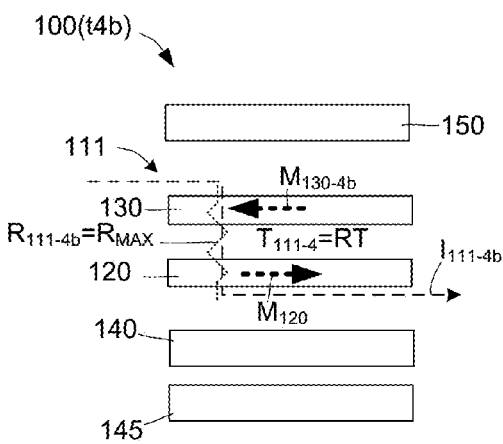

Referring to the lower portion of FIG. 2, a readout phase of the sensor operating cycle is performed after completion of the gas sensing phase. As indicated in block 231, in cases where control heat is used to maintain MTJ element 111 at the work point temperature, the readout phase begins by terminating the production of control heat, thereby allowing MTJ temperature to drop to a low temperature that precludes further detection of the target gas. In cases where external magnetic field F2 is utilized during the gas sensing phase, it is then terminated (block 233). The presence of target gas G above the predetermined minimum gas concentration level is then determined, for example, by way of reading the final resistance state of MTJ element 111 (block 217). Referring to FIGS. 3(E) and 3(F), in one embodiment this readout process is performed by re-coupling MTJ element 11 to the fixed read voltage source (i.e., voltage $V_{111}$, see FIG. 1), and then measuring the resulting read current $I_{1111-4x}$ (i.e., current $I_{111-4a}$ if FIG. 3(E) and current $I_{111-4b}$ in FIG. 3(F)) passing through MTJ element 111. In addition, according to a presently preferred embodiment, the initial readout process is conducted after MTJ element has cooled substantially to room temperature (indicated in FIGS. 3(E) and 3(F) by "$T_{111-4}$=RT") before measuring read current $I_{111-4x}$. As indicated in FIG. 3(E), when the final resistance state $R_{111-4a}$ has not switched (e.g., when the resistance value of final resistance state $R_{111-4a}$ remains low/$R_{MIN}$ because storage magnetic orientation $M_{130-4a}$ remains parallel to reference magnetic orientation $M_{120}$), read current $I_{111-4a}$ has a relatively high current level. Conversely, as indicated in FIG. 3(F), when the final resistance state $R_{111-41D}$ switched (e.g., when the resistance value of final resistance state $R_{111-4a}$ is high/$R_{MAX}$ because storage magnetic orientation $M_{130-4b}$ switches to an anti-parallel direction relative to reference magnetic orientation $M_{120}$), corresponding read current $I_{111-4b}$ has a relatively low current level. Thus, the final resistance values $R_{111-4a}$ and $R_{111-4b}$ in each case can be determined by way of determining the high/low current level of corresponding read currents $I_{111-4a}$ and $I_{111-4b}$.

Referring to the bottom of FIG. 2, in one embodiment on-chip circuitry (e.g., gas level processing sub-circuit 173, see FIG. 1) is utilized to generate measured gas concentration level data in accordance with the switched/non-switched final resistive state $R_{111}$ determined during the readout phase. As indicated in FIG. 1, in one specific embodiment, gas level processing sub-circuit 173 configured to receive read current measurement data from MTJ element measurement sub-circuit 171, to determine the high/low resistance state of resistance state $R_{111}$ using the read current measurement data, and then to generate measured gas concentration level data is generated in a form that can be transmitted (output) to and utilized by an external system. In another embodiment, the final resistance value may be determined by way of comparing the final read current (i.e., currents $I_{111-4a}$ or $I_{111-4b}$, shown in FIGS. 3(E) and 3(F), respectively) with the initial read current $I_{111-2}$ (FIG. 3(B)) generated at the end of the reset phase to determine whether the final resistance state of MTJ element 111 had switched during the gas sensing phase.

Figure 4:
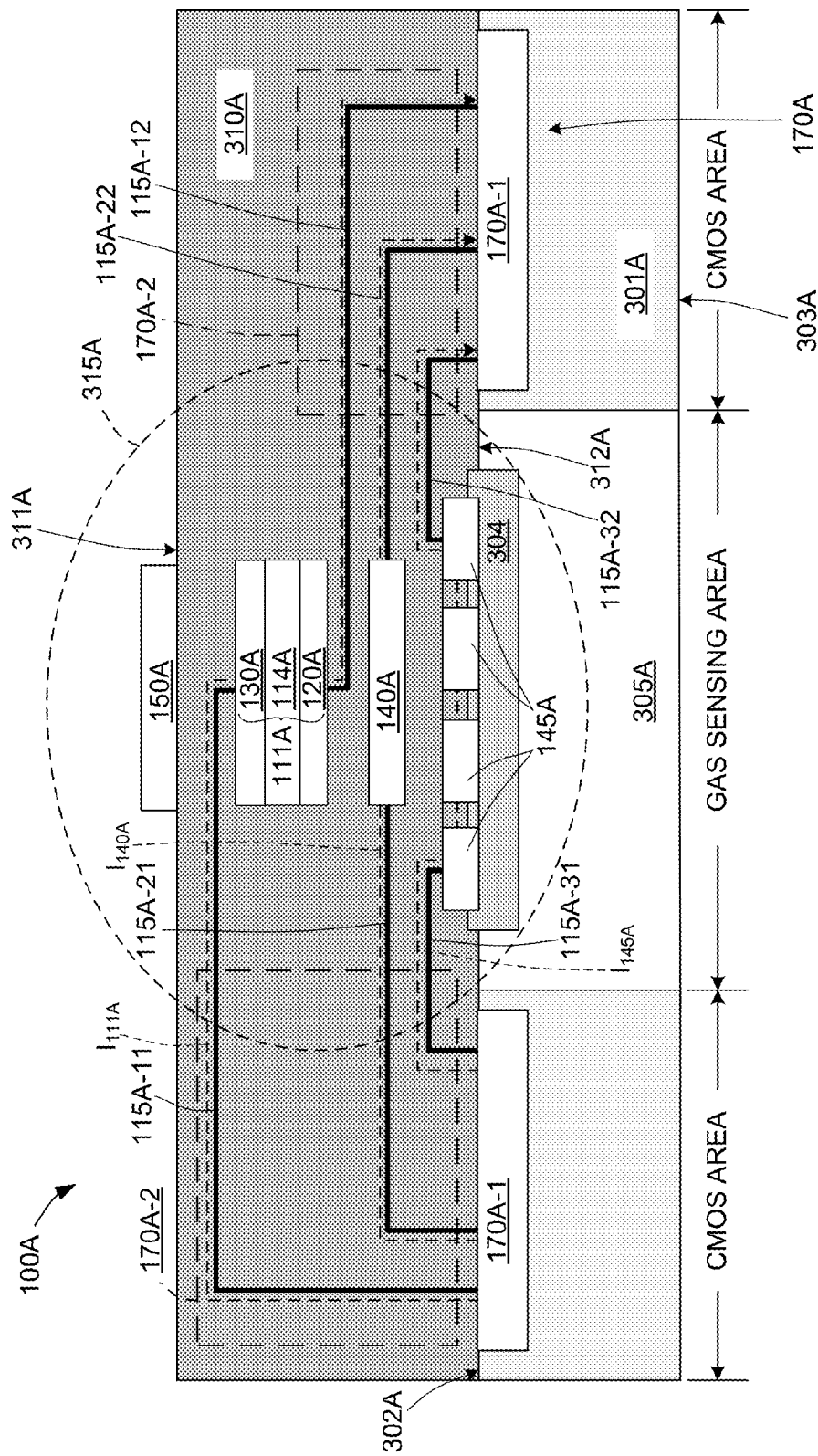
FIG. 4 is a simplified cross-sectional side view showing a membrane-type semiconductor gas sensor forming using CMOS fabrication techniques according to an exemplary embodiment of the present invention.

FIG. 4 is a simplified cross-sectional view showing a gas sensor 100A according to an exemplary practical embodiment of the present invention. Gas sensor 100A is functionally essentially identical to gas sensor 100 of FIG. 1, so for brevity various simplifications are utilized to minimize repeating description provided above. For example, various elements of gas sensor 100A that are functionally identical to corresponding elements of gas sensor 100 are identified using the same reference number with the postscript letter A (e.g., MTJ element 111A of gas sensor 100A is understood as being functionally and structurally the same as MTJ element 111 of gas sensor 100), and it is understood that details provided above regarding elements of gas sensor 100 apply to the corresponding elements of gas sensor 100A. In addition, the control circuit of gas sensor 100A is referenced as including frontend circuit structures 170A-1 and backend structures 170A-2 for reasons explained below, but it is understood that the control circuit of gas sensor 100A includes the same sub-circuits discussed above with reference to gas sensor 100.

Referring to FIG. 4, sensor 100A differs from gas sensor 100 in that gas sensing element 150A and MTJ elements 111A are fabricated on a membrane structure 135A utilizing a modified CMOS fabrication flow that achieves superior performance by providing thermal isolation between the high reaction temperatures occurring at gas sensing element 150A and the current measurement transistors forming the control circuit of gas sensor 100A. Specifically, frontend structures 170A-1 of the control circuit (e.g., NMOS and CMOS transistors) are fabricated on a bulk monocrystalline silicon substrate 301A using substantially standard CMOS frontend processing techniques in a region (lateral area) of the CMOS IC structure forming gas sensor 100A that is identified in FIG. 4 as "CMOS AREA", and then backend structures 170A-2 of the control circuit (e.g., metallization lines, vias and contacts) are fabricated in a back end stack 310A formed on the silicon substrate 301A over the frontend structures 170A-1, also in accordance with standard CMOS fabrication techniques. The standard CMOS backend process flow and, in some cases, the latter part of the standard CMOS frontend process flow, is/are modified to facilitate fabricating MTJ element 111A, gas sensing element 150A, field line structure 140A, heating element 145A, and any other sensor elements (e.g., temperature sensors) that function to generate the thermal-reaction-type gas sensing operation in separate lateral area of the CMOS IC structure identified in FIG. 4 as "GAS SENSING AREA" that is disposed next to region CMOS AREA. In one embodiment, heating element structure 145A is fabricated on FOX or STI 304A on an upper surface 302A of bulk silicon substrate 301A using the same materials that are used in front end processing (e.g. polycrystalline silicon, Titanium (Ti), Tungsten (W), silicoses, etc.) that are used during frontend processing, then (third) metal lines 115A-31 and 115A-32 are formed, e.g., using metallization layer M1, that extend between regions GAS SENSING AREA and CMOS AREA (i.e., onto membrane structure 305A) to provide signal lines for transmitting heater current $I_{145A}$ between the CMOS control circuit (e.g., frontend structures 170A-1) and heating element 145A. Field line structure 140A is formed in back end stack 310A over heating element 145A using one of the metallization layers (e.g., M1 or M2) between passivation layers, and (second) metal lines 115A-21 and 115A-22 are formed, e.g., using metallization layers M1 to M3, that extend between regions GAS SENSING AREA and CMOS AREA (i.e., onto membrane structure 305A) to provide signal lines for transmitting field line current $I_{140A}$ between frontend structures 170A-1 and field line structure 140A. MTJ element 111A is then formed, along with (first) metal lines 115A-11 and 115A-12 that extend across membrane structure 315A to provide signal lines for transmitting read current $I_{111A}$ between frontend structures 170A-1 and MTJ 111A. Finally, gas sensing element 150A is formed on an upper surface 311A of back end stack layer 310A, over MTJ element 111A. After backside processing is completed, a cavity 305A is formed below lateral area GAS SENSING AREA by way of wet or dry etching through a lower substrate surface 303A of bulk silicon substrate 301A, with the etching controlled to stop at FOX or STI 304A disposed below heating element 145A, whereby the portion of back end stack 310A located over cavity 305A defines thermally isolated membrane structure 315A. In the embodiment shown in FIG. 4, membrane structure 305A is formed as a closed-type membrane, which minimizes the number of process steps needed to form the membrane structure. In an alternative embodiment (not shown), a suspended membrane structure is formed using an additional mask that is required to form holding arms that suspend the membrane structure. In either case, membrane structure 315A is formed with a small thermal mass that facilitates rapidly setting the temperature of sensor 100A, and also serves to avoid heating control circuitry 170A-1 during sensor operation. Moreover, because gas sensor 100A is fabricated using only a few changes to otherwise standard CMOS fabrication process flow, gas sensor 100A is produced at substantially lower cost than conventional SOI-based gas sensors. That is, although the fabrication of MTJ sensing elements during back end processing of a core CMOS process flow requires the addition of three masks to the core CMOS process flow, this modification is significantly less than the cost of using SOI substrates as a starting material, and thus allows fabricating gas sensors that not only have performance advantages over conventional devices, but are also cheaper than competing solutions.

Figure 5:
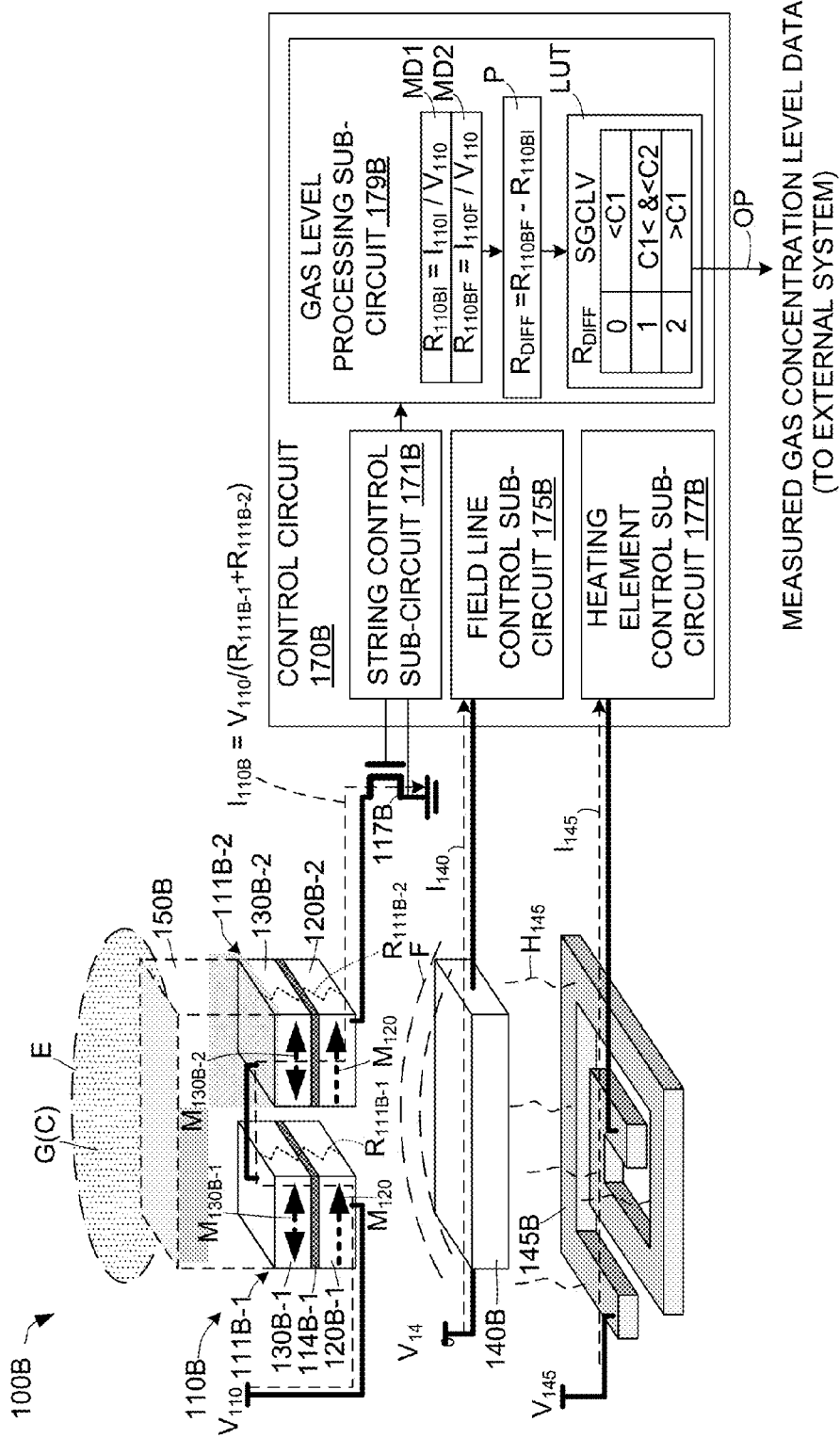
FIG. 5 is a simplified perspective view showing a semiconductor gas sensor including multiple MTJ elements according to another exemplary embodiment of the present invention.

FIG. 5 is a simplified perspective view showing a semiconductor gas sensor 100B including two MTJ elements 111B-1 and 111B-2 that are configured in the manner described above with reference to MTJ element 111 (FIG. 1) and are operably coupled to a gas sensing element 150A such that, similar to the first embodiment mentioned above, each MTJ element 111B-1 and 111B-2 switches its associated resistance state ($R_{111B-1}$ and $R_{111B-2}$, respectively) in response to an ambient concentration level C of a target gas G in an environment E containing gas sensor 100B. For example, MTJ element 111B-1 includes a storage layer 130B-1 separated from a reference layer 120B-1 by a tunnel dielectric layer 114B-1, where storage layer 130B-1 and reference layer 120B-1 comprise multi-layer structures configured to switch from an initial magnetic orientation (e.g., parallel) to an opposite (e.g., anti-parallel) magnetic orientation when gas sensing element 150A is exposed to target gas G having a concentration level above a predetermined concentration level. Gas sensor 100B also includes a control circuit 170B that is configured to implement an operating cycle similar to that described above in order to determine final resistance values of resistance states $R_{111B-1}$ and $R_{111B-2}$ after each gas sensing phase, for example, by way of controlling a field line structure 140B and a heating element 145B that are constructed and function in a manner similar to that described above with reference to gas sensor 100.

According to a novel feature of gas sensor 100B, gas sensor 100B is configured such that, during the gas sensing phase of the sensor operating cycle, resistance state $R_{111B-1}$ of MTJ element 111B-1 switches at a relatively low (first) corresponding target gas concentration level, and resistance state $R_{111B-2}$ of MTJ element 111B-2 switches at a relatively high (second) target gas concentration level—that is, MTJ element 111B-1 switches at a corresponding gas concentration level that is different from that of MTJ element 111B-2. By configuring gas sensor 100B such that MTJ elements 111B-1 and 111B-2 switch at different corresponding gas concentration levels, gas sensor 100B is configured to quantitatively determine an actual (i.e., currently measured) gas concentration level to within gas concentration level range defined by the respective switching concentration levels at which MTJ element 111B-1 and 111B-2 switch their resistance states. That is, as explained below with reference to FIGS. 7(A) to 7(C), identifying the switched/not-switched status of each MTJ element 111B-1 and 111B-2 after a gas sensing phase indicates whether the actual gas concentration level is below the relatively low target gas concentration level at which MTJ element 111B-1 switches its resistance state, between the relatively low and relatively high target gas concentration levels at which MTJ elements 111B-1 and 111B-2 respectively switch resistance states, or above the relatively high target gas concentration level. This concept is also scalable to provide highly accurate gas concentration level measurements by way of increasing the number of MTJ elements that switch resistance states at respective different gas concentration levels, and setting the respective different gas concentration levels such that the gas concentration range between each adjacent pair of respective different gas concentration levels is vanishingly small (i.e., such that the difference between the storage blocking temperatures of the MTJ elements is very small).

According to a novel feature of gas sensor 100B, field line structure 140B is operably magnetically coupled to both MTJ elements 111B-1 and 111B-2 such that, when actuated, field line structure 140B generates a magnetic field F having a sufficiently strong magnetic bias force to simultaneously bias the storage magnetic orientations of the storage layers of both MTJ elements 111B-1 and 111B-2 in accordance with a magnetic direction of magnetic field F. In one embodiment, shared field line structure 140B consists of a single integral metal structure that extends linearly under the MTJ elements 111B-1 and 111B-2, and is controlled by way of an applied read line current $I_{140}$ generated by field line control sub-circuit 175B of control circuit 100B. Because a single magnetic field F simultaneously controls both MTJ elements 111B-1 and 111B-2, field line structure 140B is effectively "shared" by MTJ elements 111B-1 and 111B-2, and therefore differs from other MTJ arrangements (e.g., magnetic logic unit (MLU) devices that require separately controlled field lines for each MTJ element). Note that the "shared" field line arrangement utilized by gas sensor 100B is expandable to any number of MTJ elements by aligning the MTJ elements linearly and/or by configuring "shared" field line structure 140B to apply a common magnetic bias force onto all of the MTJ elements. By utilizing shared field line structure 140B to control MTJ elements 111B-1 and 111B-2 (or a larger number of MTJ elements), only a single field line control signal is required to control multiple MTJ elements during the gas sensor's operating cycle, thereby reducing control circuit complexity. Further, because any number of MTJ elements can be controlled using a single shared field line, gas sensors of the present invention implementing this shared field line approach are scalable to include any number of MTJ elements without requiring additional signal lines or other modifications to the control circuitry, thereby facilitating scalable quantitative gas concentration measurement resolution without increasing operating complexity. Of course, multiple field lines could be used in place of shared field line 140B, each controlling one MTJ element.

Note that gas sensor 100B differs from gas sensor 100 (FIG. 1) in that gas sensing element 150B is not necessarily restricted to a thermal-reaction-type gas sensing element, and may be implemented using one or more a chemical-reaction-type gas sensing elements. In each case, gas sensing element 150B is operably coupled to MTJ elements 111B-1 and 111B-2, and functions to effect resistance state switching in response to corresponding gas concentration levels. In the case where gas sensing element 150B is implemented using one or more thermal-reaction-type gas sensing element, gas sensing element 150B is operably thermally coupled to MTJ elements 111B-1 and 111B-2, and reaction heat generated by gas sensing element 150B is used to cause switching of resistance states $R_{111B-1}$ and $R_{111B-2}$ of MTJ elements 111B-1 and 111B-2, respectively, in a manner similar to that described above with reference to gas sensor 100. In the case where gas sensing element 150B is implemented using one or more chemical-reaction-type gas sensing elements, gas sensing element 150B is operably physically coupled to MTJ elements 111B-1 and 111B-2 such that changes in the composition or chemical structure of gas sensing element 150B in response to adsorption of target gas G causes switching of resistance states $R_{111B-1}$ and $R_{111B-2}$ of MTJ elements 111B-1 and 111B-2, respectively.

According to another novel feature of gas sensor 100B, MTJ elements 111B-1 and 100B-2 are disposed in a series-connected NAND-type string 110B, which in the exemplary embodiment is connected between voltage source $V_{110}$ and ground by way of a select transistor 117B such that a read current $I_{140}$ passes sequentially through MTJ elements 111B-1 and 100B-2. With this arrangement, series-connected string 110B exhibits a total string resistance $R_{110B}$, that is collectively defined by (i.e., in this example, a sum of) corresponding respective resistance values $R_{111B-1}$ and $R_{111B-2}$ of MTJ elements 111B-1 and 111B-2. In a manner similar to that described above, control circuit 170B includes a string control sub-circuit 171B that functions to generate and measure read current $I_{140}$ during reset and readout operations, thereby providing both an initial string resistance value $R_{111BI}$ and a final string resistance value $R_{111BI}$ that can be used to determine the individual resistance states $R_{111B-1}$ and $R_{111B-2}$ of MTJ elements 111B-1 and 111B-2. In the illustrated embodiment, control circuit 170B utilizes a gas sensing processing sub-circuit 179B including memory devices MD1 and MD2 for respectively storing resistance values $R_{111BI}$ and $R_{111BI}$, a processor P configured to calculate a difference $R_{DIFF}$ between the initial and final resistance values, and a lookup table LUT configured to store predetermined gas concentration level data values SGCLV. With this arrangement, calculated difference value $R_{DIFF}$ (e.g., 0, 1 or 2) is utilized to access a corresponding gas concentration level value stored in lookup table LUT (i.e., less than lower value C1, between values C1 and C2, or above value C2), and the corresponding gas concentration level value is then transmitted as the output measured gas concentration level data via an output port OP to an external system (not shown).

Figure 6:
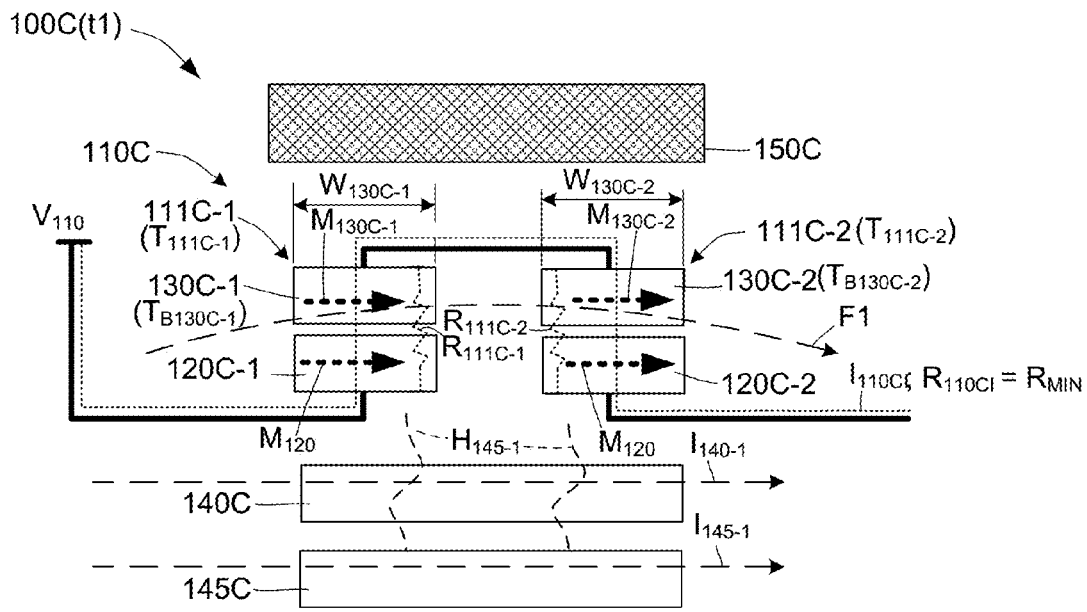
FIG. 6 is a simplified side views showing a thermal-reaction-type gas sensor including multiple MTJ elements according to another exemplary embodiment of the present invention.

FIG. 6 shows a thermal-reaction-type semiconductor gas sensor 100C including two MTJ elements 111C-1 and 111C-2 that are operably thermally coupled to a thermal-reaction-type gas sensing element 150A and connected in a series-connected string 110C. Similar to gas sensor 100B, each MTJ element 111C-1 and 111C-2 is consistent with MTJ element 111 of FIG. 1, and switches its associated resistance state $R_{111C-1}$ and $R_{111C-2}$ in response to different ambient target gas concentration level. In addition, gas sensor 100C includes a shared field line structure 140C and a shared heating element 145C that function in the manner described above.

According to a feature of gas sensor 100C, MTJ elements 111C-1 and 111C-2 are maintained at substantially identical temperatures during the sensor operating cycle, and are configured to switch at different gas concentration levels by way of having respective storage layers 130C-1 and 130C-2 that exhibit different storage blocking temperatures $T_{B130C-1}$ and $T_{B130C-2}$ respectively (e.g., wherein storage blocking temperature $T_{B130C-1}$ is 25° C. lower than storage blocking temperature $T_{B130C-2}$). That is, shared heating element 145C and gas sensing element 150A are respectively thermally coupled and otherwise configured to respectively generate control and reaction heat in a manner similar to that described above, but in this case the heat is generated such that MTJ temperature $T_{111C-1}$ and $T_{111C-2}$ of MTJ elements 111C-1 and 111C-2, respectively, are maintained at essentially identical temperature levels during the reset and gas sensing phases. Providing MTJ elements 111C-1 and 111C-2 with different storage blocking temperatures $T_{B130C-1}$ and $T_{B130C-2}$ can be achieved by way of intentional and/or non-intentional (inherent) mechanisms. For example, in the exemplary embodiment shown in FIG. 6, MTJ elements 111C-1 and 111C-2 are intentionally provided with different storage blocking temperatures $T_{B130C-1}$ and $T_{B130C-2}$ by way of controlling the applied fabrication process used to produce gas sensor 100C such that each MTJ element 111C-1 and 111C-2 respectively has a different lateral size $W_{111C-1}$ and $W_{111C-2}$. In one embodiment, lateral sizes $W_{111C-1}$ and $W_{111C-2}$ vary in the range of 100 nm and 500 nm. In other embodiments, different storage blocking temperatures are intentionally achieved by forming MTJ elements having different anti-ferromagnetic (AFM) layer thickness. In yet other embodiments, the MTJ elements are generated using the same processing parameters (e.g., same lateral width and thickness), and inherent blocking temperature distributions, which typically vary in the range of 50-100° C. due to fluctuations of the grain sizes in the AFM layers forming the storage and/or reference layers, are utilized to provide the desired different storage blocking temperatures.

Figure 7A:
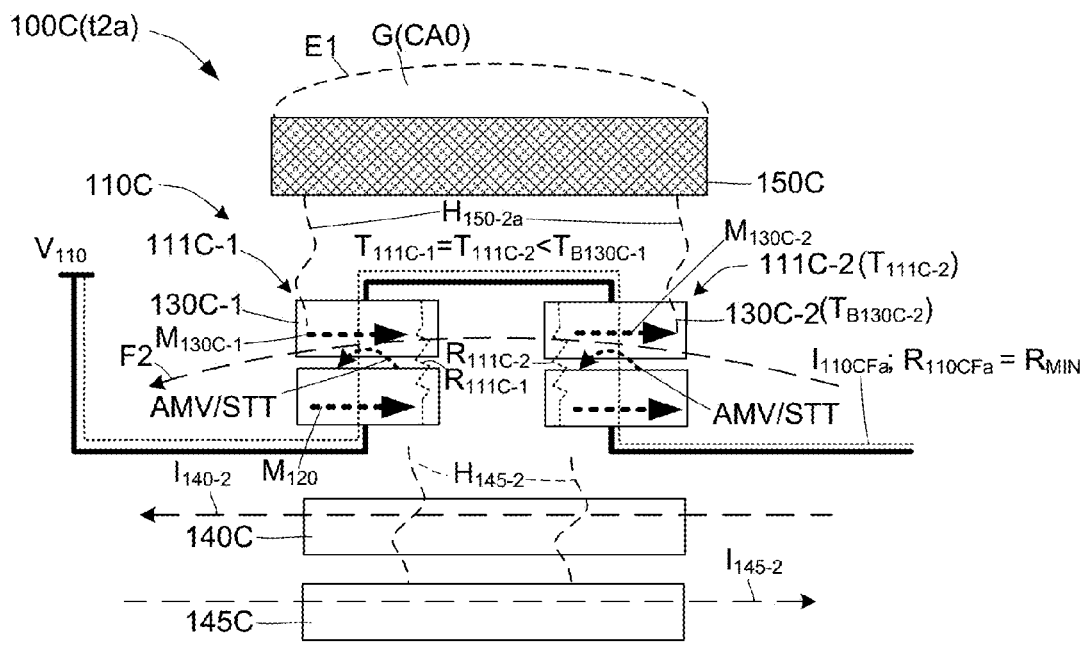
FIGS. 7(A), 7(B) and 7(C) are simplified side views showing the gas sensor of FIG. 6 during different gas sensing phases.
Figure 7B:
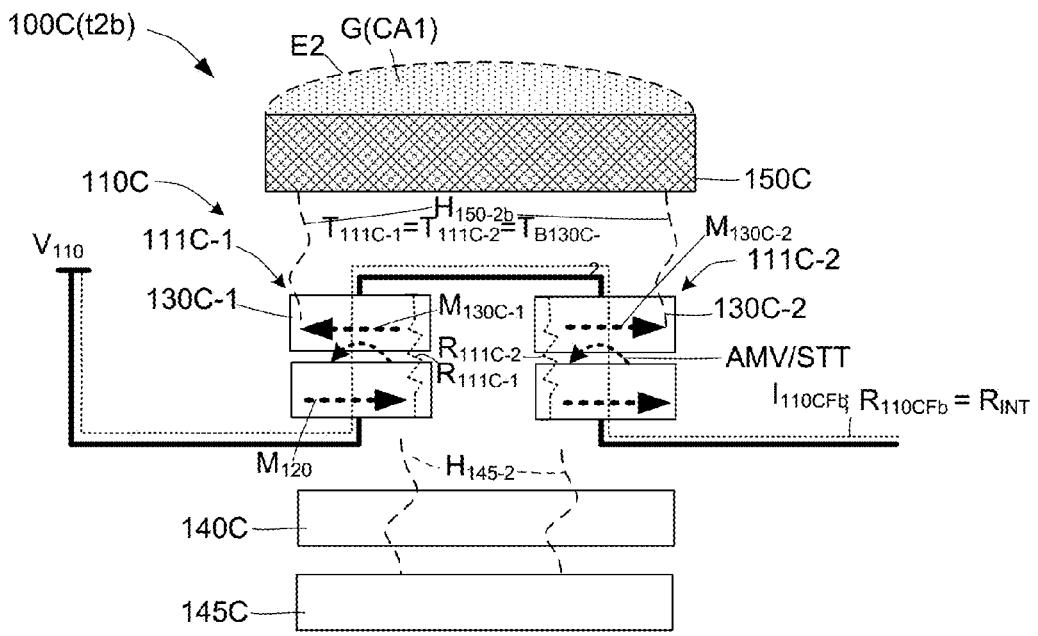
Figure 7C:
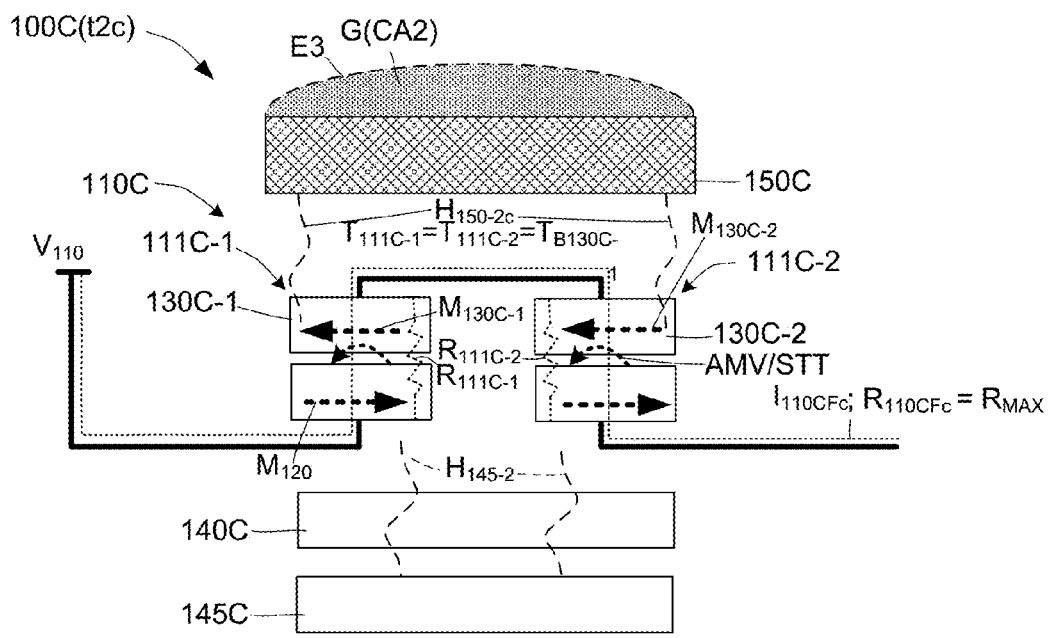

An exemplary operation cycle of gas sensor 100C is depicted with reference to FIGS. 6 and 7(A) to 7(C), where FIG. 6 shows gas sensor 100C during a reset phase (i.e., at a time t1), and FIGS. 7(A) to 7(C) depict gas sensor 100C during alternative gas reaction phases (i.e., at a time t2 after time t1) in which gas sensor 100C is exposed to three different target gas concentration levels CA0, CA1 and CA2, respectively (i.e., FIG. 7(A) depicts gas sensor 100C exposed to target gas concentration CA0 at associated time t2a, FIG. 7(B) depicts gas sensor 100C exposed to target gas concentration CA1 at associated time t2b, and FIG. 7(C) depicts gas sensor 100C exposed to target gas concentration CA2 at associated time t2c).

Referring to FIG. 6, during the reset phase a first amount of control heat $H_{145-1}$ is generated (e.g., by actuating heating element 145C using a first heating current $I_{145-1}$) such that MTJ temperatures $T_{111C-1}$ and $T_{111C-2}$ of MTJ elements 111C-1 and 111C-2 increase above both associated storage blocking temperatures $T_{B130C-1}$ and $T_{B130C-2}$, and then field line structure 140C is activated (e.g., by way of a first field line current $I_{140-1}$) to generate a magnetic field F1, whereby storage magnetic orientations $M_{130C-1}$ and $M_{130C-2}$ of storage layers 130C-1 and 130C-2, respectively, are biased into parallel (first) directions relative to reference magnetic orientations $M_{120}$ of reference layers 120C-1 and 120C-2. At the end of the reset phase, MTJ elements 111C-1 and 111C-2 are cooled below both associated storage blocking temperatures $T_{B130C-1}$ and $T_{B130C-2}$ (preferably to room temperature), whereby storage magnetic orientations $M_{130C-1}$ and $M_{130C-2}$ are fixed in the parallel direction, and an initial resistance value $R_{110CI}$ of series-connected string 110C is determined, e.g., by way of measuring a read current $I_{110CI}$ that is generated using methods described above (note that read current $I_{110CI}$ is generated after the reset operation, but is indicated in FIG. 6 for reference). In one embodiment, initial resistance value $R_{110CI}$ is stored in an on-chip memory location (e.g., memory device MD1, shown in FIG. 5). In this case, because both MTJ elements 111C-1 and 111C-2 are fixed in parallel directions, initial resistance value $R_{110CI}$ has a minimum resistance value $R_{MIN}$.

FIGS. 7(A) to 7(C) depict gas sensor 100C exposed to target gas concentration levels CA0, CA1 and CA2, respectively, during alternative gas reaction phases. Referring to FIG. 7(A), the gas sensing phase involves heating MTJ elements 111C-1 and 111C-2 to a work point temperature (and subsequently maintaining MTJ elements 111C-1 and 111C-2 at the work point temperature) while applying a magnetic bias force such that at least one of storage magnetic orientations $M_{130C-1}$ and $M_{130C-2}$ switches from the parallel (first) direction to an anti-parallel (second) direction when target gas G is present in environment E in an amount above a predetermined minimum gas concentration level. Increasing/maintaining the temperature of MTJ elements 111C-1 and 111C-2 to/at the work point temperature involves re-activating heating element 145C by way of an associated heater current $I_{145-2}$ such that control heat $H_{145-2}$ maintains MTJ temperatures $T_{110-1}$ and $T_{111C-2}$ at the work point temperature, which is described in additional detail below with reference to FIG. 8. Applying the opposite magnetic bias force involves operating gas sensor 100C such that storage magnetic orientations $M_{130C-1/2}$ are biased in the anti-parallel direction relative to reference magnetic orientations $M_{120}$ by a magnetic bias force directed opposite to the magnetic bias force applied during the reset phase. In one embodiment, the magnetic bias force utilized during the gas sensing phase is generated using anti-parallel magnetization force AMV, spin torque transfer STT and/or by generating a (second) external field F2, where using magnetic force AMV requires configuring MTJ elements 111C-1 and 111C-2 in the manner described above, and generating a (second) external field F2 involves, for example, passing a field line current $I_{140-2}$ along field line 140C in a direction opposite to field line current $I_{140-1}$ during the reset phase (see FIG. 6). Under these conditions, as explained below with reference to the examples shown in FIGS. 7(A) to 7(C), at least one of storage magnetic orientations $M_{130C-1}$ and $M_{130C-2}$ is caused to switch from the initial parallel direction to the anti-parallel (opposite) direction when target gas G is above the predetermined minimum gas concentration level corresponding to storage blocking temperature $T_{B130C-1}$ of MTJ element 111C-1.

FIG. 7(A) shows gas sensor 100(t2a) during a first exemplary gas sensing phase in which gas sensing element 150C is exposed to an environment E1 containing target gas G in a relatively low (or zero) concentration level CA0. As mentioned above, MTJ elements 111C-1 and 111C-2 are increased/maintained at the work point temperature by way of control heat $H_{145-2}$ generated by heating element 145C. Target gas concentration level CA0 causes gas sensing element 150C to generate reaction heat $H_{150-2a}$ that either fails to increase MTJ temperatures $T_{111C-1}$ and $T_{111C-1}$ above the work point temperature, or raises MTJ temperatures $T_{111C-1}$ and $T_{111C-1}$ by an amount that remains below storage blocking temperature $T_{B130C-1}$ of MTJ element 111C-1. Because neither MTJ element reaches its storage blockage temperature, storage magnetic orientations $M_{130C-1}$ and $M_{130C-2}$ remain fixed in the parallel direction relative to reference magnetic orientation $M_{120C}$ (i.e., resistance states $R_{111C-1}$ and $R_{111C-2}$ retain low resistance values).

FIG. 7(B) shows gas sensor 100(t2b) during an alternative (second) exemplary gas sensing phase in which gas sensing element 150C is exposed to an environment E2 containing target gas G in a concentration level CA1 corresponding to the predetermined minimum gas concentration level of MTJ element 111C-1. As in the first example, MTJ elements 111C-1 and 111C-2 are increased/maintained at the work point temperature by way of control heat $H_{145-2}$ generated by heating element 145C. In this case, target gas concentration level CA1 causes gas sensing element 150C to generate reaction heat $H_{150-2b}$ in an amount that raises MTJ temperatures $T_{111C-1}$ and $T_{111C-1}$ to storage blocking temperature $T_{B130C-1}$ of MTJ element 111C-1, whereby the applied magnetic bias force STT/F2 causes storage magnetic orientation $M_{130C-1}$ to switch from the parallel direction to the anti-parallel direction relative to reference magnetic orientation $M_{120C}$, whereby resistance state $R_{111C-1}$ of MTJ element 111C-1 changes from its initial low resistance value to a high resistance value. Because MTJ element 111C-2 remains below storage blocking temperature $T_{B130C-2}$, resistance state $R_{111C-2}$ retains its initial low resistance value.

FIG. 7(C) shows gas sensor 100(t2c) during an alternative (third) exemplary gas sensing phase in which gas sensing element 150C is exposed to an environment E3 containing target gas G in a relatively high concentration level CA2 corresponding to the predetermined minimum gas concentration level of MTJ element 111C-2. As in the previous examples, MTJ elements 111C-1 and 111C-2 are increased/maintained at the work point temperature by way of control heat $H_{145-2}$ generated by heating element 145C. Target gas concentration level CA2 causes gas sensing element 150C to generate reaction heat $H_{150-2c}$ in an amount that raises MTJ temperatures $T_{111C-1}$ and $T_{111C-1}$ to storage blocking temperature $T_{B130C-2}$ of MTJ element 111C-2. Because MTJ elements 111C-1 and 111C-2 both reach temperatures above their respective storage blocking temperatures, both storage magnetic orientations $M_{130C-1}$ and $M_{130C-2}$ switch from parallel to anti-parallel directions relative to reference magnetic orientation $M_{120c}$, whereby resistance states $R_{111C-1}$ and $R_{111C-2}$ of MTJ elements 111C-1 and 111C-2 change from low to high resistance values.

After each of the alternative gas sensing phases described above with reference to FIGS. 7(A) to 7(C), MTJ elements 111C-1 and 111C-2 are cooled substantially to room temperature (e.g., until MTJ temperatures $T_{111C-1}$ and $T_{111C-2}$ are approximately 25° C.), and a readout phase is then performed to determine the final string resistance value and to generate/output corresponding measured gas concentration level data. Similar to the readout processes described above, reading final string resistance is achieved by applying a fixed read voltage and measuring the resulting read current. As indicated in FIG. 7(A), because neither MTJ element 111C-1 and 111C-2 switched resistance states during the gas sensing phase in response to gas concentration level CA0, read current $I_{110CFa}$ generated during the readout phase is substantially at the same high current level as that of read current $I_{110CI}$, which was generated at the end of reset (see FIG. 6), so final string resistance value $R_{110CFa}$ is also equal to minimum resistance value $R_{MIN}$. In contrast, referring to FIG. 7(B), because MTJ element 111C-1 switched its resistance state during the gas sensing phase in response to gas concentration level CA1, read current $I_{110CFb}$ has a level that is lower than read current $I_{110CI}$ by an amount corresponding to the increased resistance state of one MTJ element, final string resistance value $R_{110CFb}$ is assigned an intermediate value $R_{INT}$. Referring to FIG. 7(C), because both MTJ elements switched resistance states in response to gas concentration level CA2, read current $I_{110CFc}$ has a level corresponding to the increased resistance state of two MTJ elements, final string resistance value $R_{110CFc}$ is assigned a maximum resistance value $R_{MAX}$. Generating and outputting measured gas concentration level data is then generated, for example, using the process described above with reference to gas level processing sub-circuit 179B (FIG. 5).

Figure 8:
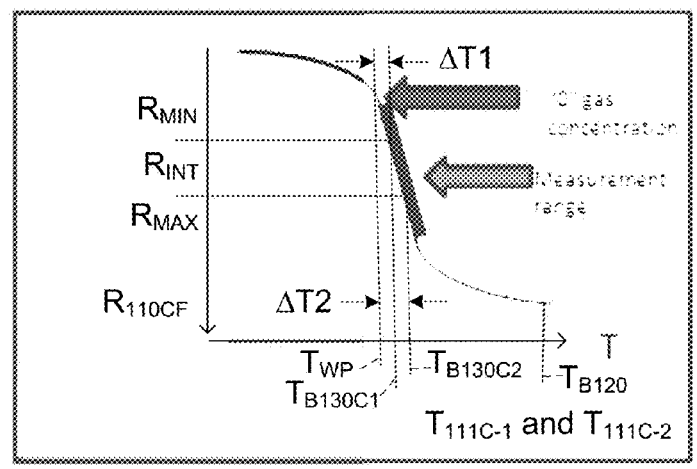
FIG. 8 is resistance versus temperature graph illustrating operating principles of the thermal-reaction-type gas sensor of FIG. 6.

FIG. 8 is simplified graph that relates MTJ temperatures $T_{111C-1}$ and $T_{111C-2}$ and total string resistance $R_{110C}$ during the exemplary gas sensing phase of gas sensor 100C described above with reference to FIGS. 7(A) to 7(C), and in particular illustrates exemplary work point temperature $T_{WP}$ (i.e., zero target gas concentration point) in relation to storage blocking temperatures $T_{B130C-1}$ and $T_{B130C-2}$, and the corresponding measurement range of gas sensor 100C. As discussed above, work point temperature $T_{WP}$ is generally defined as the lowest temperature at which gas sensing element 150C (e.g., FIG. 7(A)) generates reaction heat in response to a selected target gas (i.e., the zero gas concentration level). That is, if gas sensor 100C is at temperature below the work point temperature, gas sensing element 150C would not react to the presence of the selected target gas. Also, for sensor 100C to function properly, MTJ elements 111C-1 and 111C-2 (e.g., FIG. 7(A)) must have corresponding storage blocking temperatures $T_{B130C-1}$ and $T_{B130C-2}$ that are above work point temperature $T_{WP}$. The temperature differences required to change the total string resistance of string 110C are indicated in FIG. 8 as $\Delta T1$ and $\Delta T2$, where temperature difference $\Delta T1$ is the difference between work point temperature $T_{WP}$ and storage blocking temperature $T_{B130C-1}$, and is therefore relatively small in comparison to temperature difference $\Delta T2$ between work point temperature $T_{WP}$ and storage blocking temperature $T_{B130C-2}$. Applying the graphic description of FIG. 8 to the exemplary gas sensing phase of FIG. 7(A), when gas sensor 100C is exposed to target gas G below concentration level CA1 (i.e., level CA0), reaction heat $H_{150C-2a}$ generated by gas sensing element 150C increases MTJ temperatures $T_{111C-1}$ and $T_{111C-2}$ by an amount less than $\Delta T1$ (i.e., by an amount insufficient to increase from the work point temperature to storage blocking temperature $T_{B130C-1}$), whereby neither MTJ element 111B-1 switches its resistance state, leaving string resistance $R_{111CFa}$ at $R_{MIN}$. Referring to FIG. 7(B), when gas sensor 100C is exposed to target gas G at concentration level CA1, reaction heat $H_{150C-2b}$ generated by gas sensing element 150C is sufficient to increase MTJ temperatures $T_{111C-1}$ and $T_{111C-2}$ by amount $\Delta T1$ from the work point temperature to storage blocking temperature $T_{B130C-1}$, whereby only MTJ element 111B-1 switches its resistance state, changing string resistance $R_{111CFb}$ to $R_{MIN}$. Referring to FIG. 7(C), when gas sensor 100C is exposed to target gas G at concentration level CA2, reaction heat $H_{150c-2c}$ is sufficient to increase MTJ temperatures $T_{111C-1}$ and $T_{111C-2}$ by amount $\Delta T2$ from the work point temperature to storage blocking temperature $T_{B130C-2}$, whereby both MTJ elements 111B-1 and 111B-2 switches resistance states, changing string resistance $R_{111CFc}$ to $R_{MAX}$.

Figure 9:
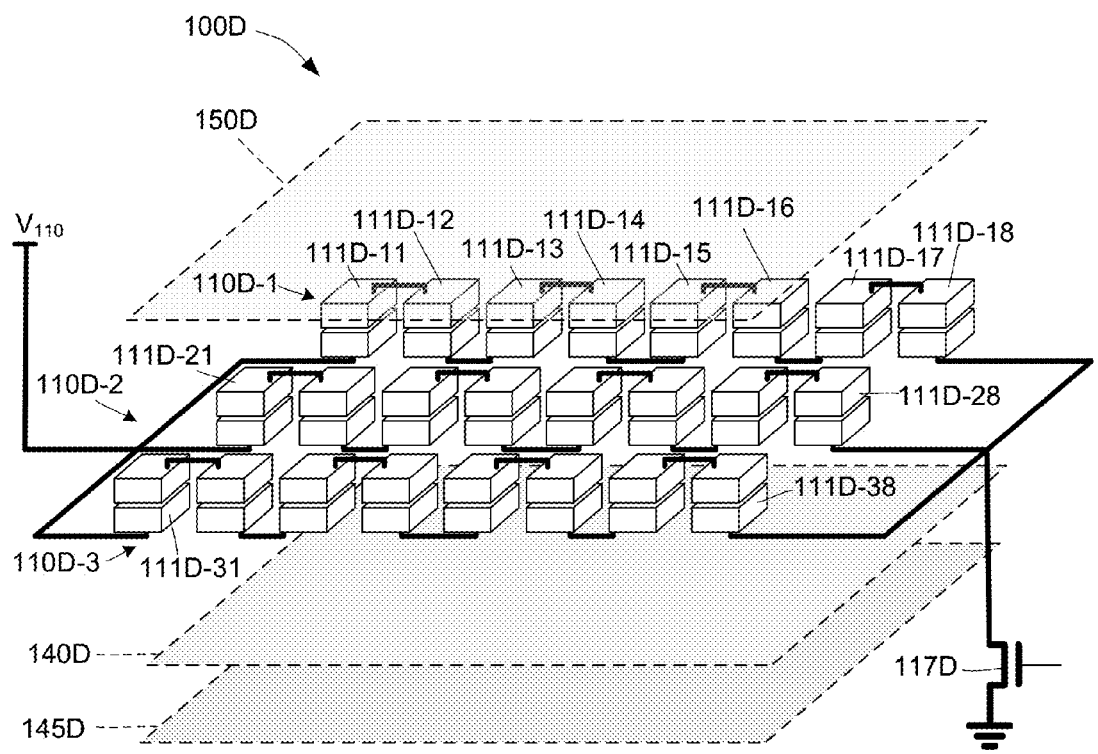
FIG. 9 is simplified diagram showing multiple MTJ element strings connected in parallel according to another embodiment of the present invention.

FIG. 9 depicts a gas sensor 100D including MTJ elements disposed in three series-connected strings 110D-1, 110D-2 and 110D-3 that are also connected in parallel between a voltage source $V_{110}$ and a select transistor 117D. Each string 110D-1 includes multiple MTJ elements that are configured to switch at different gas concentration levels (e.g., string 110D-1 includes MTJ elements 111D-11 to 111D-18, string 110D-2 includes MTJ elements 111D-21 to 111D-28, and string 110D-3 includes MTJ elements 111D-31 to 111D-38), where each of the MTJ elements is configured as described above. Gas sensor 100D also includes a gas sensing element 150D, a field line 140D and a heating element 145D that are depicted in simplified form for clarity. Gas sensor 100D illustrates one example of how gas sensors of the present invention are readily scalable to provide a range of measurement accuracies by way of increasing the number of MTJ elements in each series-connected string and/or connecting multiple series strings in parallel, thereby providing gas sensors capable of measuring very small gas concentration level variations. Note that the total string resistance of each parallel series-connected string 111D-1 to 111D-3 is collectively defined by a sum of each strings MTJ elements 111D-11 to 111D-18, 111D-21 to 111D-28 and 111D-31 to 111D-38, respectively, and that a total resistance of the entire parallel-connected-string structure is also collectively defined by the MTJ elements of the three strings. The parallel-connected-string arrangement also facilitates measuring multiple target gases, where each target gas has a different combustion temperature (i.e., the temperature corresponding to the "0" gas concentration level of FIG. 8). In this case, gas sensor 100D may be implemented to measure, for example, three different target gases by way of actuating heating element 145D to heat the parallel-connected-string structure to a first predetermined gas concentration level optimized to measure a first target gas having a measurement range corresponding to storage blocking temperatures of MTJ elements 111D-11 to 111D-18 of string 110D-1, then heating the parallel-connected-string structure to a second (higher) predetermined gas concentration level optimized to measure a second target gas having a measurement range corresponding to storage blocking temperatures of MTJ elements 111D-21 to 111D-28 of string 110D-2, and then heating the parallel-connected-string structure to a third (yet higher) predetermined gas concentration level optimized to measure a third target gas having a measurement range corresponding to storage blocking temperatures of MTJ elements 111D-31 to 111D-38 of string 110D-3.

Figure 10:
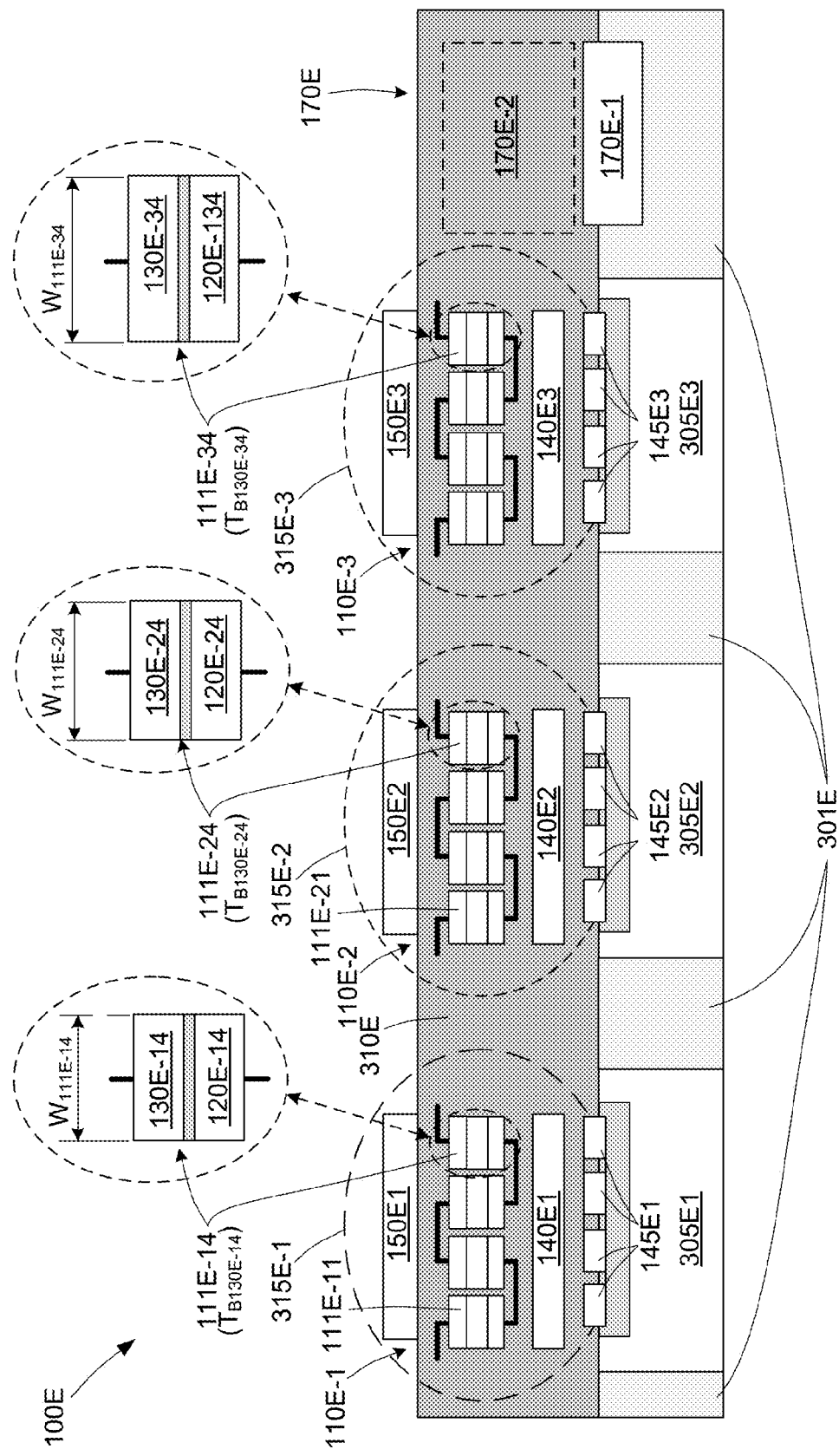
FIG. 10 is a simplified cross-sectional side view showing a semiconductor gas sensor including multiple string-based membrane-type sensor regions according to an exemplary embodiment of the present invention.

FIG. 10 depicts a gas sensor 100E including a CMOS control circuit 170E made up of frontend structures 170E-1 disposed on a silicon substrate 301E and backend structures 170E-2 disposed in a back end stack 310E formed on the silicon substrate 301E, and multiple MTJ elements 111E-11 to 111E-34 and three gas sensing elements 150E-1 to 150E-3 respectively disposed in groups on membrane structures 315E-1 to 315E-3. Similar to the embodiment described above with reference to FIG. 4, each membrane structure 315E-1 to 315E-3 comprises a respective portion of back end stack 310E and is disposed over a corresponding cavity 305E-1 to 305E-3 defined in silicon substrate 301E. In the disclosed embodiment, the groups of MTJ elements respectively disposed on membrane structures 315E-1 to 315E-3 are series-connected in NAND-type strings 110E-1 to 110E-3 that are respectively magnetically coupled to shared field line structures 140E-1 to 140E-3 and thermally coupled to associated heat sensing elements 150E-1 to 150E-3 and heating elements 145E-1 to 145E-3.

Specifically, membrane structure 315E-1 includes series-connected string 110E-1 including MTJ elements 111E-11 to 111E-14 that are magnetically coupled to shared field line structure 140E-1 and thermally coupled to associated heat sensing element 150E-1 and heating element 145E-1, membrane structure 315E-2 includes string 110E-2 including MTJ elements 111E-21 to 111E-24, shared field line structure 140E-2, heat sensing element 150E-2 and heating element 145E-2, and membrane structure 315E-3 includes string 110E-3 including MTJ elements 111E-31 to 111E-34, shared field line structure 140E-3, heat sensing element 150E-3 and heating element 145E-3. In addition, gas sensor 100E is configured to simultaneously quantitatively measure three different target gases by way of configuring each group of MTJ elements to switch resistance states in response to different storage blocking temperatures, and by configuring each heating element 145E-1 to 145E-3 to maintain corresponding groups of MTJ elements at a different work point temperature. To optimize the MTJ elements for the different work point temperatures, in one embodiment each group of MTJ elements is formed with a different lateral size. For example, as indicated by the bubbles at the top of FIG. 10, MTJ element 111E-14 is formed with a lateral size $W_{111E-14}$ that is smaller than lateral size $W_{111E-24}$ of MTJ element 111E-24 in order to provide MTJ element 111E-14 with a lower storage blocking temperature $T_{B130E-14}$ than MTJ element 111E-24, and lateral size $W_{111E-24}$ of MTJ element 111E-24 is smaller than $W_{111E-34}$ of MTJ element 111E-34 to provide MTJ element 111E-24 with a lower blocking temperature $T_{B130E-24}$ than storage blocking temperature $T_{B130E-34}$ of MTJ element 111E-34. Other approaches mentioned above may also be used to generate MTJ elements having different storage blocking temperatures.

Although the present invention has been described with respect to certain specific embodiments, it will be clear to those skilled in the art that the inventive features of the present invention are applicable to other embodiments as well, all of which are intended to fall within the scope of the present invention.

The invention claimed is:

1. A gas sensor for quantitatively determining a concentration of a target gas in an environment, the gas sensor comprising:
a plurality of magnetic tunnel junction (MTJ) elements, each of said plurality of MTJ elements including a reference layer defining an associated reference magnetic orientation and a storage layer defining an associated storage magnetic orientation, wherein said storage layer of each of said plurality of MTJ elements is configured such that said associated storage magnetic orientation is switchable between a parallel direction and an anti-parallel direction relative to said associated reference magnetic orientation, whereby a corresponding resistance state of each of said plurality of MTJ elements is respectively switchable between a first resistance value and a second resistance value;
a gas sensing element operably coupled to said plurality of MTJ elements such that said gas sensing element causes a first corresponding resistance state of a first MTJ element to switch from one of said first and second resistance values to the other of said first and second resistance values only when said concentration of said target gas in said environment is at least equal to a first concentration level during a gas sensing phase, and said gas sensing element causes a second corresponding resistance state of a second MTJ element to switch from said one of said first and second resistance values to said other of said first and second resistance values only when said concentration level of said target gas is at least equal to a second concentration level during said gas sensing phase, said second concentration level being higher than said first concentration level; and a control circuit configured to determine final resistance values of said first and second corresponding resistance states after said gas sensing phase.

2. The gas sensor of claim 1, further comprising a field line structure operably magnetically coupled to said plurality of MTJ elements, wherein said control circuit is further configured to control the field line structure such that said field line structure generates a magnetic field configured to simultaneously bias the storage magnetic orientations of the storage layers of all of said plurality of MTJ elements in accordance with a magnetic direction of the magnetic field.

3. The gas sensor of claim 1, wherein said gas sensing element comprises one of a thermal-reaction-type gas sensing element and a chemical-reaction-type gas sensing element.

4. The gas sensor of claim 1, wherein said gas sensing element comprises a thermal-reaction-type gas sensing element operably thermally coupled to said plurality of MTJ elements and configured to generate reaction heat in an amount proportional to an actual concentration level of said target gas when said gas sensing element contacts said environment, and wherein said first MTJ element is configured such that first corresponding resistance state only switches resistance values when a first MTJ temperature of said first MTJ element is above a first storage blocking temperature, wherein said second MTJ element is configured such that second corresponding resistance state only switches resistance values when a second MTJ temperature of said second MTJ element is above a second storage blocking temperature, said second storage blocking temperature being greater than said first storage blocking temperature, and wherein said gas sensor is configured such that said reaction heat generated by said thermal-reaction-type gas sensing element increases said first and second MTJ temperatures to said first storage blocking temperature when said actual concentration level of said target gas is at least equal to said first concentration level during said gas sensing phase, and such that said reaction heat increases said first and second MTJ temperatures to said second storage blocking temperature when said actual concentration level of said target gas is at least equal to said second concentration level during said gas sensing phase.

5. The gas sensor of claim 4, wherein said first and second MTJ elements are further configured such that a first lateral size of said first MTJ element is smaller than a second lateral size of said second MTJ element.

6. The gas sensor of claim 4, further comprising a heating element operably thermally coupled to said plurality of MTJ elements, wherein said control circuit is further configured to actuate said heating element such that during a reset operating phase, said control heat generated by said heating element increases said first and second MTJ temperatures above said first and second storage blocking temperatures, and during said gas sensing operating phase, said control heat generated by said heating element maintains said first and second MTJ temperatures below said first storage blocking temperature.

7. The gas sensor of claim 1, wherein said plurality of MTJ elements are disposed in a series-connected string such that a total string resistance of said series-connected string is collectively defined by the corresponding resistance values of said plurality of MTJ elements, and wherein said control circuit configured to determine final resistance values of said first and second corresponding resistance states using a read current passed through said series-connected string.

8. The gas sensor of claim 7, further comprising a field line structure operably magnetically coupled to said plurality of MTJ elements, wherein said control circuit is further configured to control the field line structure such that said field line structure generates a magnetic field having sufficient magnetic force to simultaneously bias the storage magnetic orientations of the storage layers of all of said plurality of MTJ elements in accordance with a magnetic direction of the magnetic field.

9. The gas sensor of claim 7, wherein said plurality of MTJ elements are disposed in a plurality of series-connected strings, and such that the plurality of series-connected strings are connected in parallel.

10. The gas sensor of claim 7, wherein said control circuit comprises a CMOS control circuit including frontend structures disposed on a silicon substrate and backend structures disposed in a back end stack formed on the silicon substrate, wherein said plurality of MTJ elements and said gas sensing element are disposed on a first membrane structure comprising a first portion of said back end stack that is disposed over a first cavity defined in said silicon substrate.

11. The gas sensor of claim 10, further comprising a second plurality of MTJ elements and a second gas sensing element disposed on a second membrane structure comprising a second portion of said back end stack that is disposed over a second cavity defined in said silicon substrate, wherein each MTJ element of said second plurality of MTJ elements has a second lateral size that is larger than a first lateral size of each of said plurality of MTJ elements disposed on said first membrane structure.

* * * * *